United States Patent [19]

Hanna et al.

[11] Patent Number: 5,284,477
[45] Date of Patent: Feb. 8, 1994

[54] DEVICE FOR CORRECTING THE SHAPE OF AN OBJECT BY LASER TREATMENT

[75] Inventors: Khalil Hanna, Paris; Louis Asfar, Le Chesnay, both of France; Jean-Claude Chastang, Mahopac, N.Y.

[73] Assignee: International Business Machine Corporation, Armonk, N.Y.

[21] Appl. No.: 874,204

[22] Filed: Apr. 27, 1992

Related U.S. Application Data

[63] Continuation of Ser. No. 570,981, Aug. 23, 1990, abandoned, which is a continuation of Ser. No. 211,055, Jun. 24, 1988, abandoned.

[30] Foreign Application Priority Data

Jun. 25, 1987 [FR] France ............... 87 08963

[51] Int. Cl.$^5$ ............................................. A61N 5/06
[52] U.S. Cl. ............................................ 606/5; 606/10; 606/12; 606/13; 219/121.6; 219/121.67; 219/121.73; 219/121.74; 219/121.8
[58] Field of Search ............ 128/395, 397, 398; 606/2-6, 10-13; 219/121.6, 121.61, 121.67, 121.68, 121.73, 121.74, 121.75, 121.78, 121.80

[56] References Cited

U.S. PATENT DOCUMENTS

| | | | |
|---|---|---|---|
| 4,579,430 | 4/1986 | Bille | 128/633 |
| 4,584,424 | 5/1986 | Vaguine | 128/804 |
| 4,648,400 | 3/1987 | Schneider et al. | 128/303.1 |
| 4,665,913 | 5/1987 | L'Esperance | 128/395 |

FOREIGN PATENT DOCUMENTS

| | | | |
|---|---|---|---|
| 3535073 | 4/1987 | Fed. Rep. of Germany ... | 128/303.1 |
| 8705794 | 10/1987 | World Int. Prop. O. ....... | 128/303.1 |

OTHER PUBLICATIONS

"A Rotating Slit Delivery System for Excimer Laser Refractive Keratoplasty" by Hanna et al; Am. J. Ophthal. Mar. 1987, p. 474.
"Excimer Laser Refractive Keratoplasty" by Hanna et al; Nov. 1986 pp. 1-16.

Primary Examiner—David M. Shay
Attorney, Agent, or Firm—Nixon & Vanderhye

[57] ABSTRACT

The invention concerns a device for correcting the shape of an object by laser treatment.

The device comprises means (1) for emitting a laser beam (FL) and means (2) for generating a treatment laser beam (FLT) comprising at least one lobe of elongate cross-section. Means (3) enable focussing of the image of the lobe or lobes of the treatment laser beam on the area of the object (OE) to be corrected and means (4) enable displacement of the image of the lobe of the treatment laser beam in translation or in rotation over the area of the object to be corrected. The total correction or ablation is effected by the summation of a plurality of elementary discrete ablations.

Application to refractive surgery in the case of keratomileusis for myopia, hypermetropia or astigmatism, and to shaping contact lenses and intra-ocular implants.

15 Claims, 12 Drawing Sheets

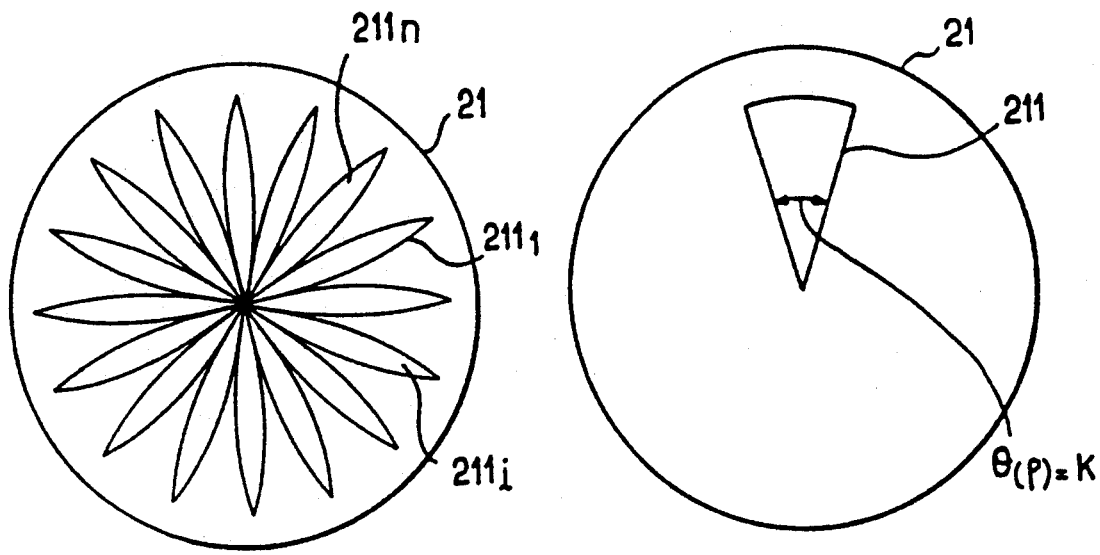
FIG_3d  FIG_3e
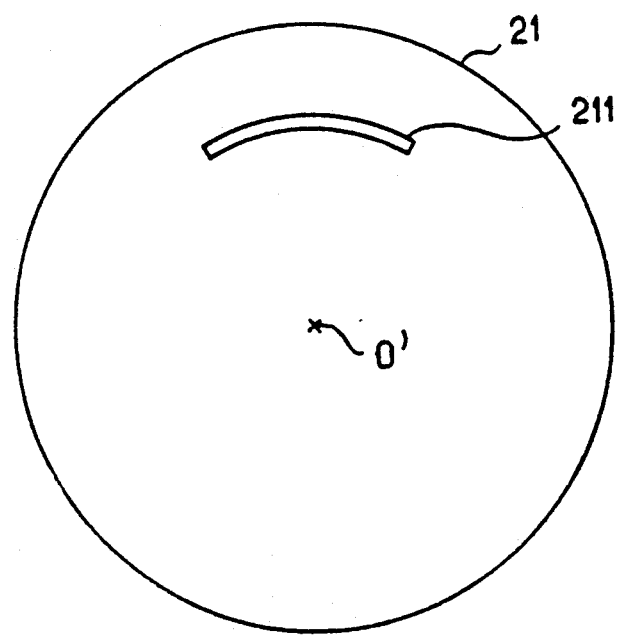
FIG_3f

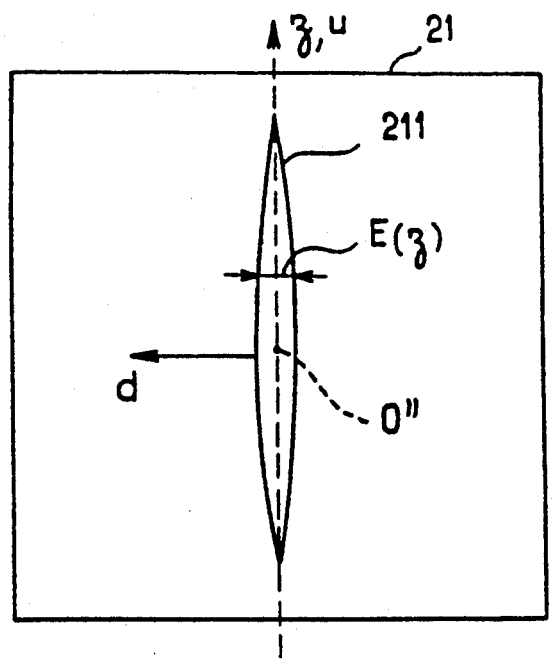
FIG_4b
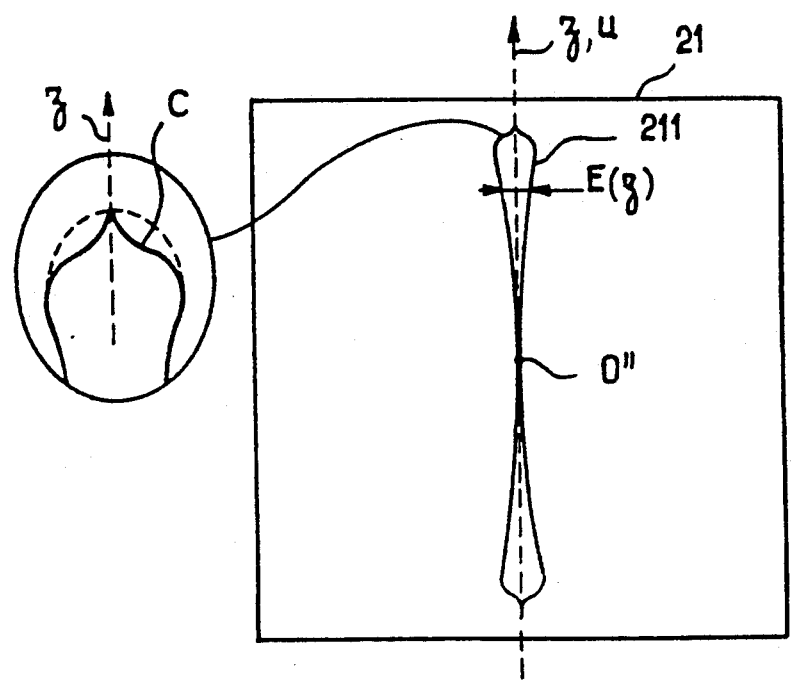
FIG_4c

FIG_6c

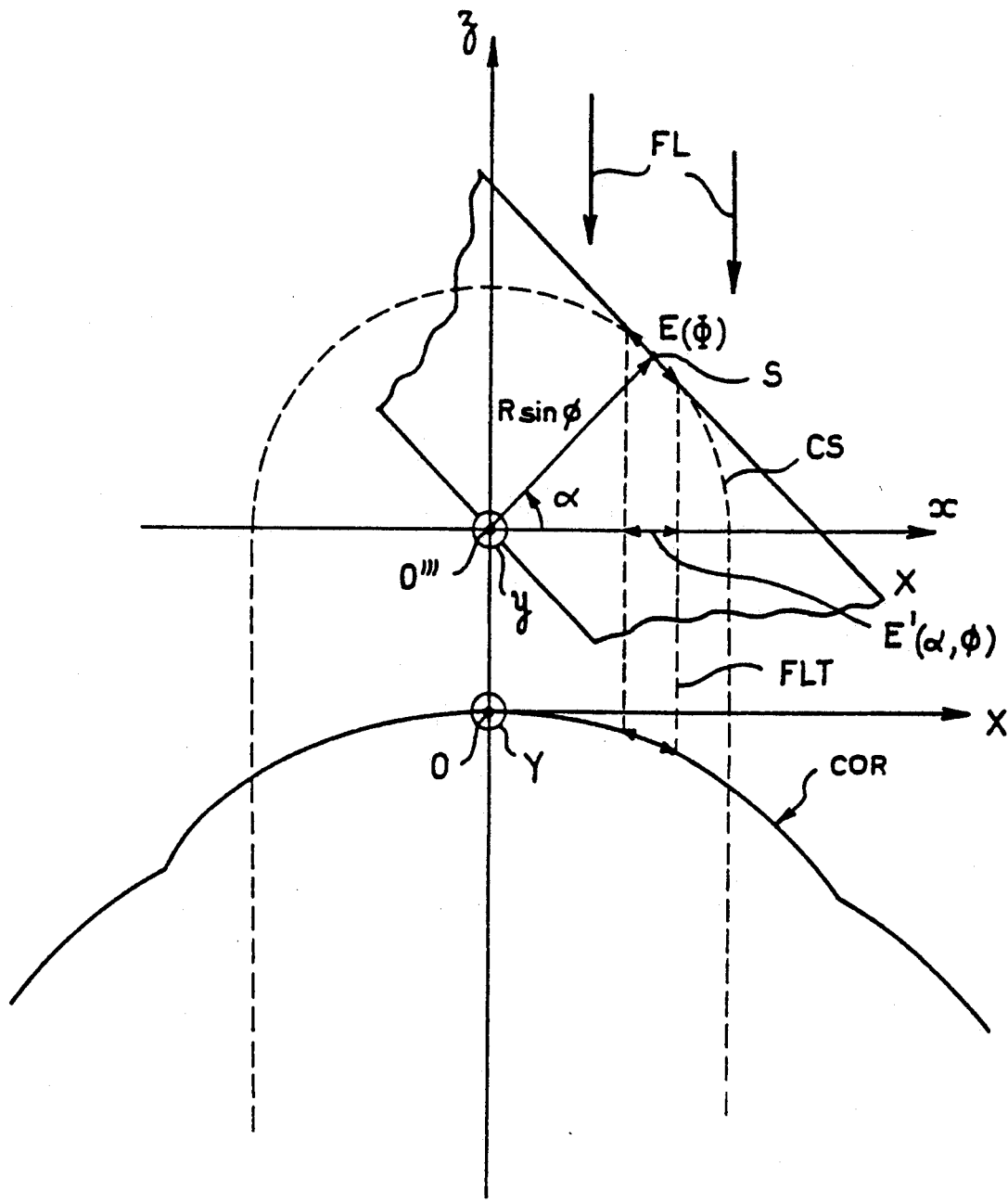
FIG_6e

DEVICE FOR CORRECTING THE SHAPE OF AN OBJECT BY LASER TREATMENT

This is a continuation of application Ser. No. 07/570,981, filed Aug. 23, 1990, now abandoned, which is a continuation of application Ser. No. 07/211,055 filed Jun. 24, 1988, now abandoned.

BACKGROUND OF THE INVENTION

1. Field of the Invention

The present invention relates to a device for performing surgery on the cornea of the eye.

2. Discussion of Prior Art

The purpose of such modifications of the shape of the cornea is to correct ametropia by correcting dimensional optical characteristics of the cornea and principally its radius of curvature. At the present time such modifications, known as keratomileusis, are achieved by actually machining a disk removed from the cornea. The disk is made rigid by freezing it and then machined by the Barraquer process or applied to a template with the appropriate radius of curvature and recut using the Barraquer-Krumeich technique.

This type of operation has the major disadvantage of necessitating first removal of the disk of corneal material and then treatment of the aforementioned disk, which has to be reimplanted on the eyeball of the patient after treatment.

However, recent work has shown the very precise ablative properties of excimer laser radiation when this radiation is applied to the corneal tissue. The radiation emitted by an excimer laser, with a wavelength substantially equal to 193 nm, may be used to eliminate corneal material by photodecomposition. Generally speaking, a round light spot (an image of the laser beam) is formed on the cornea, the spot being substantially centered on the optical axis of the eyeball. The spot has a substantially circular or annular shape or a symmetrical shape relative to the optical axis of the eyeball and may be moved and/or the radius/size changed, the exposure time for a particular area depending on the thickness of the cornea to be eliminated.

Although such devices enable direct operation on the eyeball of the patient, enabling better centering through avoiding the aforementioned problem of cutting out, and reimplanting after correction, a piece of the cornea, they do not make it possible to implement a precise treatment method in that, although the exposure time can be defined with good precision, the effects and in particular the thickness of the cornea subjected to photodecomposition vary with the size of the light spot and the energy density of the laser beam used. Moreover, the surface state of the cornea after treatment and undesirable side effects due to thermal or shockwave phenomena vary significantly with the energy level delivered by each pulse and the repetition frequency with which the same area is successively irradiated.

SUMMARY OF THE INVENTION

An object of the device in accordance with the present invention for performing surgery on the cornea of the eye using laser radiation is to remedy the aforementioned disadvantages through the use of a device enabling an ablation process to be carried out by successive discrete ablations, the total ablation resulting from the summation of numerous discrete ablations, while avoiding irradiating the same area with two or more consecutive pulses and limiting the surface area irradiated by each pulse.

Another object of the present invention is the use of a device in which each elementary discrete ablation is optimised both from the point of view of the extent of the area over which the discrete ablation is effected and the irradiation time for the area to carry out the aforementioned discrete ablation, the surface state of the area over which the discrete ablation has been effected featuring a minimum degree of roughness and the corrected area, the summation of the areas over which one or more discrete ablations have been effected, having a minimum degree of roughness, the reduction of undesirable side effects such as shockwave and thermal effects making it possible to preserve and respect the integrity of surrounding tissue.

Another object of the present invention is the use of a refractive surgery device for laser treatment of the cornea of the eye enabling direct operation on the eyeball of the patient, the operation being computer- or microcomputer-assisted.

The refractive surgical device for laser treatment of the cornea of the eye in accordance with the present invention comprises means for emitting a pulsed laser beam. It is characterised in that it comprises means for generating a treatment laser beam comprising at least one lobe of elongate cross-section, means for focussing the image of said lobe or lobes of the treatment laser beam onto the area of the eye to be corrected, and means for synchronising displacement of the image of said lobe or lobes of the treatment laser beam, complete correction or ablation being effected as the summation of a plurality of elementary discrete ablations.

The device in accordance with the invention finds an application in any surgical operation on the cornea of the eye intended to correct ametropia by keratomileusis in the case of myopia, hypermetropia and astigmatism, by epikeratothakia, by radiating incisions, bar-shaped incisions or circular incisions for corneal grafting, uniform deep ablation for lamellar grafting.

BRIEF DESCRIPTION OF THE INVENTION

The invention will be better understood on reading the following description and referring to the drawings in which:

FIG. 1 shows a graph plotting the depth of a discrete elementary ablation by one laser emission pulse as a function of the radiation energy density, FIG. 2a shows a plan view of the cornea of an eye with the corresponding definition of parameters defining the surface to be treated, FIG. 2b shows a view in cross-section on the line A—A in FIG. 2a with the corresponding definition of parameters defining the surface treated and the area removed by photodecomposition, FIG. 3a shows a block diagram of the device in accordance with the invention in the case where the image of the treatment laser beam is moved in rotation, FIG. 3b shows a particularly advantageous object slit enabling treatment by keratomileusis of myopia in the case of the embodiment of the device from FIG. 3a, FIG. 3c shows a particularly advantageous object slit enabling treatment by keratomileusis of hypermetropia in the case of the embodiment of the device from FIG. 3a, FIG. 3d shows in a non-limiting way one embodiment of an object slit with multiple lobes enabling treatment of myopia by keratomileusis in the same way as in the case of FIG. 3b, FIGS. 3e and 3f respectively represent in an advantageous, non-limiting way an embodiment of an auxiliary slit of the circular sector type, enabling, when associated with an object slit such as that shown in FIG. 3b or FIG. 3c, treatment by keratomileusis of astigmatism of the eyeball and the cornea, in the case of the embodiment of the device from FIG. 3a and a circular incision for trepannation and for correction of astigmatism by partial and localised incisions, FIG. 4a shows a non-limiting alternative embodiment of the device in accordance with the invention shown in FIG. 3a in the case where the image of the treatment laser beam is moved either in rotation or in translation, FIG. 4b shows a particularly advantageous object slit enabling treatment of myopia by keratomileusis in the case of the embodiment of the device from FIGS. 3a and 4a, the image of the laser beam being moved in translation, FIG. 4c shows a particularly advantageous object slit enabling treatment of hypermetropia by keratomileusis in the case of the embodiment of the device from FIG. 4a, the image of the laser beam being moved in translation, FIG. 4d shows in a non-limiting way an alternative embodiment of an object slit with multiple lobes enabling treatment of myopia by keratomileusis in the same way as in the case of FIG. 3e, FIG. 4e shows a particularly advantageous embodiment in which at least one edge of the slit is adjustable to enable compensation of irregular distribution of the energy of the laser beam, FIG. 5a shows in the case of use of the device from FIG. 4a with the image of the laser beam moved in translation the area of the cornea subjected to irradiation in two elementary areas extending in two directions OX, OY, the areas defined by movement in translation of the laser beam in the corresponding direction OX or OY being concurrent, FIG. 5b shows a profile characteristic of total ablation of a cornea subjected to treatment for myopia by keratomileusis, FIG. 5c shows a profile characteristic of total ablation of a cornea subject to treatment for hypermetropia by keratomileusis, FIGS. 6a and 6b show a non-limiting embodiment of a diaphragm enabling improved focussing of images of the slits onto the cornea and FIGS. 6c through 6e show a particularly advantageous embodiment of a diaphragm the slit in which is moved in rotation, enabling discontinuity between the corrected and non-corrected areas of the cornea to be avoided, FIG. 7 shows an advantageous alternative embodiment of the device in accordance with the invention.

DETAILED DESCRIPTION OF PREFERRED EMBODIMENTS

Prior to the description proper of the device for refractive surgical laser treatment of the cornea of the eye in accordance with the invention, there follow preliminary remarks summarising the effects of excimer laser light irradiation at a wavelength of 193 nanometers when such radiation is applied to the corneal tissue.

Figure 1:
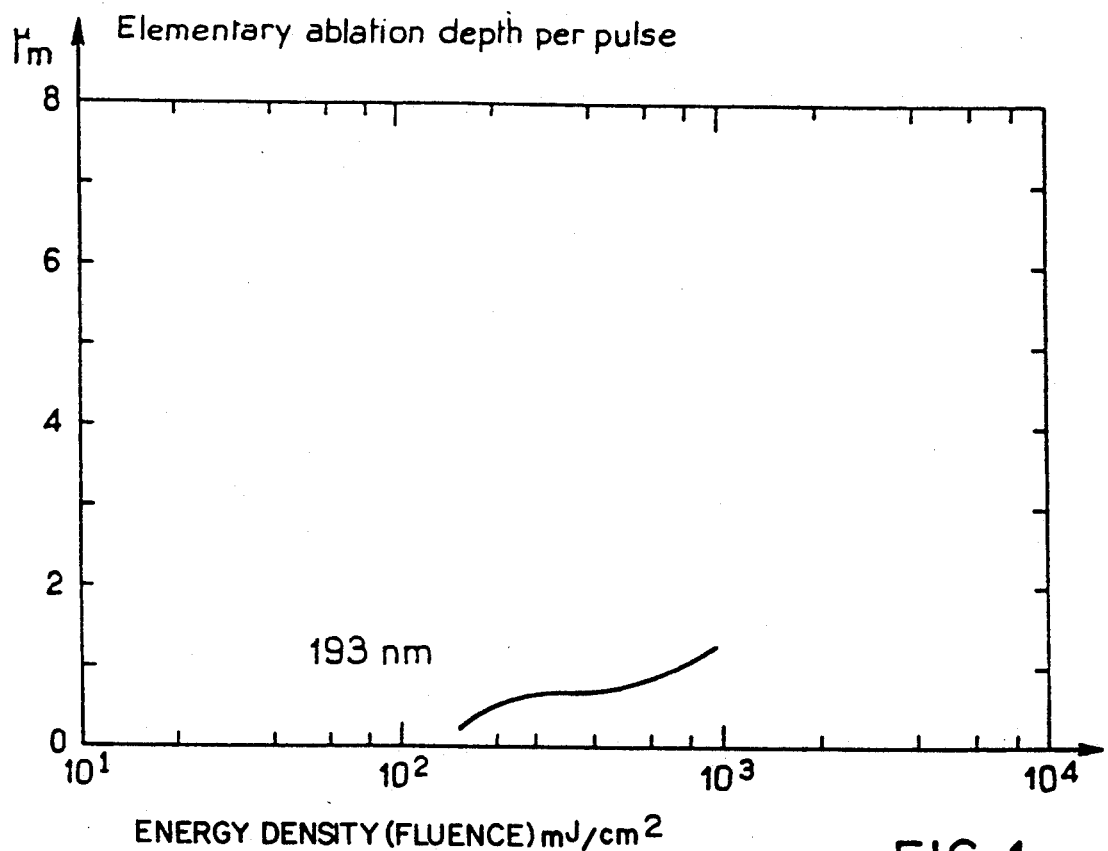

FIG. 1 shows a curve of ablation on which the values of the depth of discrete elementary ablations are plotted on the ordinate axis, this axis being graduated in micrometers, as a function of the energy density per laser illumination pulse, the abscissa axis being graduated in millijoules/cm$^2$.

The discrete elementary ablation curve is characterised by the presence of a threshold, that is to say a value of the energy density below which no ablation occurs. Generally speaking, the curve is strongly non-linear and the depth of ablation increases only very slowly with the energy density. It will in fact be noted that the depth of each discrete elementary ablation is small, lying between 0.25 and 1 $\mu$m.

The refractive eye surgery device in accordance with the invention is, in its essentials, advantageously based on a discrete ablation process, a large number of discrete elementary ablations being employed to obtain a total resulting ablation. Although the discrete elementary ablation caused by a laser illumination pulse features the previously mentioned non-linearity with regards to its depth as a function of the energy density, it is assumed (providing that the energy density is constant from one pulse to another) that the resulting total ablation at a fixed point for a given number n of consecutive pulses is equal to n times the average ablation corresponding to a single pulse. Thus the discrete elementary ablation corresponding to the aforementioned average ablation is denoted:

$$\bar{a}(e) \tag{1}$$

This average ablation corresponds substantially for a laser illumination pulse with an energy density in the order of 200 millijoules/cm$^2$ to a depth of ablation corresponding to the step in the curve shown in FIGS. 1, and in practice to a depth of ablation between 0.5 and 0.8 $\mu$m.

A more detailed description of the operations to be carried out to correct ametropia by correcting dimensional optical characteristics of the cornea and principally its radius of curvature will be given with reference to FIGS. 2a and 2b. To simplify the description of the device in accordance with the invention, the principal operations aforementioned will be limited to keratomileusis for treating myopia, hypermetropia and myopic astigmatism.

Figure 2A:
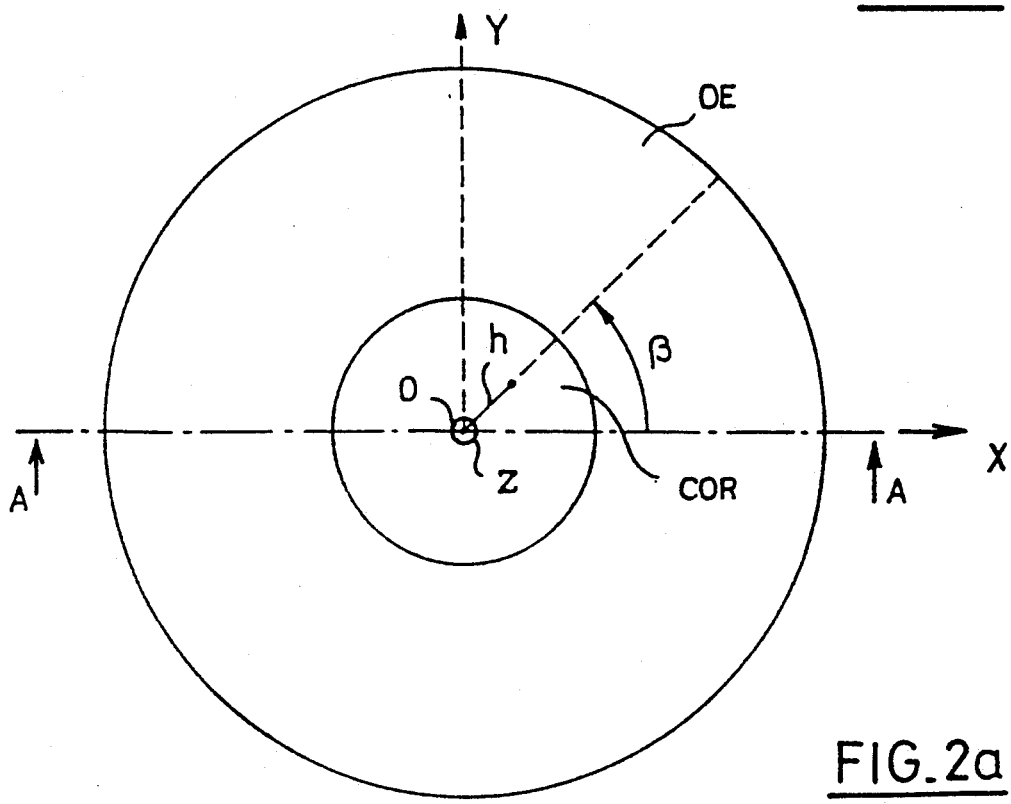

FIG. 2a shows a plan view of the eyeball designated OE. The aforementioned plan view is seen along the optical axis of the eye designated OZ in FIG. 2a, the aforementioned optical axis being centered on the cornea designated COR and the pupil of the iris, not shown in this figure. In the following explanation it will be considered that the optical axis and the visual axis of the eye are substantially coincident. Reference directions are denoted OX and OY, the frame of reference OX, OY being an orthogonal frame of reference. The distance from a given point on the corneal surface to the optical axis OZ is designated h.

Figure 2B:
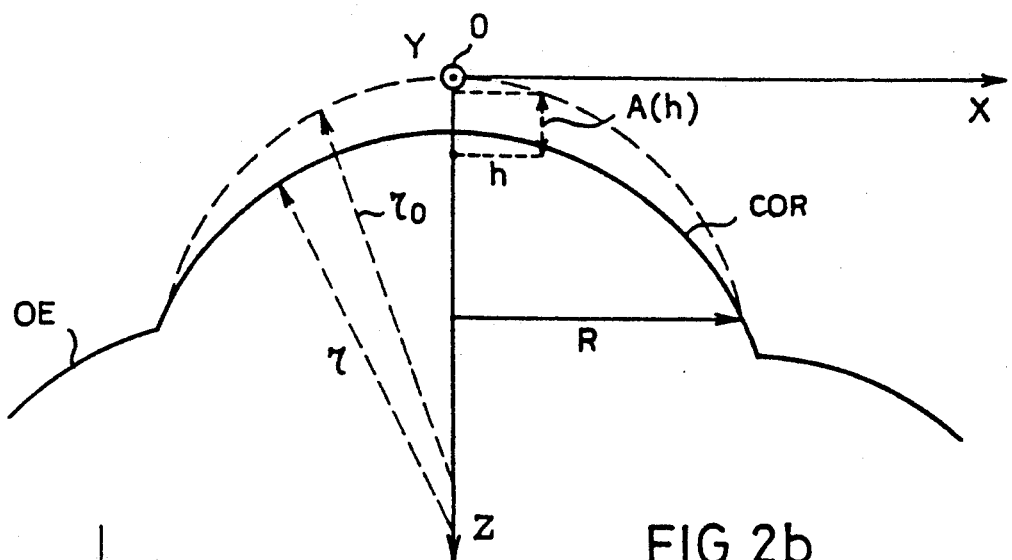

FIG. 2b shows a cross-section on the line A—A in FIG. 2a. In FIG. 2b the radius of curvature of the cornea COR before treatment, the cornea before treatment being shown in FIG. 2b in dashed outline, is designated $r_0$ while r designates the radius of curvature of the cornea COR after treatment using the device in accordance with the invention. Generally speaking, R designates the radius of the optical area on the cornea for operating on and correcting the latter. Of course, the value of this parameter R and the area of the cornea over which the operation will be carried out are defined by the practitioner, following a clinical analysis carried out by him or her. Finally, A(h) designates the ablation function, that is to say the thickness (in the direction Oz of the optical axis of the eye) to be removed by photodecomposition to a distance h from the optical axis OZ of the eye to alter the cornea from the initial radius of curvature $r_0$ to the final radius of curvature r, after the aforementioned operation.

In the case of keratomileusis for myopia, the object of the corresponding operation is to increase the radius of curvature of the cornea. The initial radius of curvature $r_0$ is increased to a value $r > r_0$ after the operation. This effect is obtained by ablation with a substantially parabolic profile of revolution and the ablation function is, using the notation from FIGS. 2a and 2b:

$$A(h) = A_0 \left( 1 - \frac{h^2}{R^2} \right); 0 \leq h \leq R \quad (2)$$

In the case of keratomileusis for hypermetropia, the object of the operation is to reduce the radius of curvature of the cornea, the initial radius $r_0$ being reduced to a value $r < r_0$. In this case ablation is still on a surface of revolution about the optical axis OZ of the eye, there being no ablation at the centre O, for h=0, and maximum ablation for a particular value $h = \nu$. The ablation of the corneal profile between $h = \nu$ and R then constitutes a merging area defined by purely mechanical considerations: no sudden transition with the optical area proper ($h < \nu$) or with the rest of the cornea ($h > R$). The ablation function A(h) satisfies the equation:

$$A(h) = A_0 \frac{h^2}{R^2} \text{ where } 0 \leq h \leq \nu \quad (3)$$

For values of h greater than $\nu$ and less than R, the ablation function A(h) is a polynomial in h defining the aforementioned merging area according to previously mentioned mechanical considerations.

In equations (2) and (3) above, $A_0$ represents, of course, the extent of ablation for h=0, that is the thickness of ablation at the optical axis OZ of the eye itself:

$$A_0 = \frac{R^2}{2} \left( \frac{1}{r_0} - \frac{1}{r} \right)$$

In the case of keratomileusis for myopic astigmatism, the ablation is no longer on a surface of revolution. It will be remembered that in cases of corneal astigmatism the principal astigmatism directions are defined by orthogonal planes in which it is possible to define a maximum radius of curvature and a minimum radius of curvature for the optical surface in question, in this instance the cornea. In this case, and by way of simplification, and in line with what the practitioner will have to do in any event to carry out the operation using the device in accordance with the invention, it is advantageous to take as the reference directions OX and OY the principal astigmatism directions as previously defined. The aforementioned directions OX and OY are then contained in the aforementioned astigmatism planes. The radius of curvature of the cornea COR is in this case a function of the azimuth angle denoted $\beta$, the radius of curvature r of the cornea after the operation for example satisfying the equation:

$$r(\beta) = r_x \cos\beta + r_y \sin\beta \quad (4)$$

In equation (4), $\beta$ represents the azimuth angle of any plane containing the optical axis OZ, the azimuth angle being for example the dihedral angle formed by the aforementioned any plane and the plane OZ, OX. The values $r_x$ and $r_y$ are the corresponding values of the radius of curvature r for $\beta=0$ and $\beta=\pi/2$, respectively.

In the case of keratomileusis for myopic astigmatism, research has shown that the ablation profile may be written (the OX and OY axes having been determined as previously described):

$$A(X,Y) = A_0 \left( 1 - \frac{X^2}{R_X^2} - \frac{Y^2}{R_Y^2} \right) \quad (5)$$

In equation (5), the quantities $A_0$, $R_x$ and $R_y$ are defined by:

$$A_0 = \frac{A_0^x + A_0^y}{2}, R_x = R\sqrt{\frac{A_0}{A_0^x}}, \text{ and } R_y = R\sqrt{\frac{A_0}{A_0^y}} \quad (6)$$

The terms $A^x_0$ and $A^y_0$ are themselves defined as functions of the parameters R, $r_x$ and $r_y$ by equations (7) and (8) below:

$$A_0^x = \frac{R^2}{2} \left( \frac{1}{r_x} - \frac{1}{r} \right) \quad (7)$$

$$A_0^y = \frac{R^2}{2} \left( \frac{1}{r_y} - \frac{1}{r} \right) \quad (8)$$

Generally speaking, iso-ablation curves are ellipses.

A more detailed description of the device in accordance with the invention for performing refractive surgery on the eye by laser treatment of the cornea will now be given with reference to FIG. 3a.

Referring to the aforementioned figure, the device in accordance with the invention comprises means 1 for emitting a laser beam denoted FL. The laser beam FL is a pulsed laser beam.

The means for emitting the laser beam FL are preferably an excimer laser emitting radiation at a wavelength of 193 nanometers. The emission means 1 preferably emit laser pulses with an energy level of the laser beam FL in the order of 180 millijoules per pulse, the repetition frequency of the laser pulses being in the order of 20 Hz. The duration of each pulse is in the order of 10 nanoseconds and the instantaneous power of each pulse reaches high values, in the order of 10 MW.

Figure 3A:
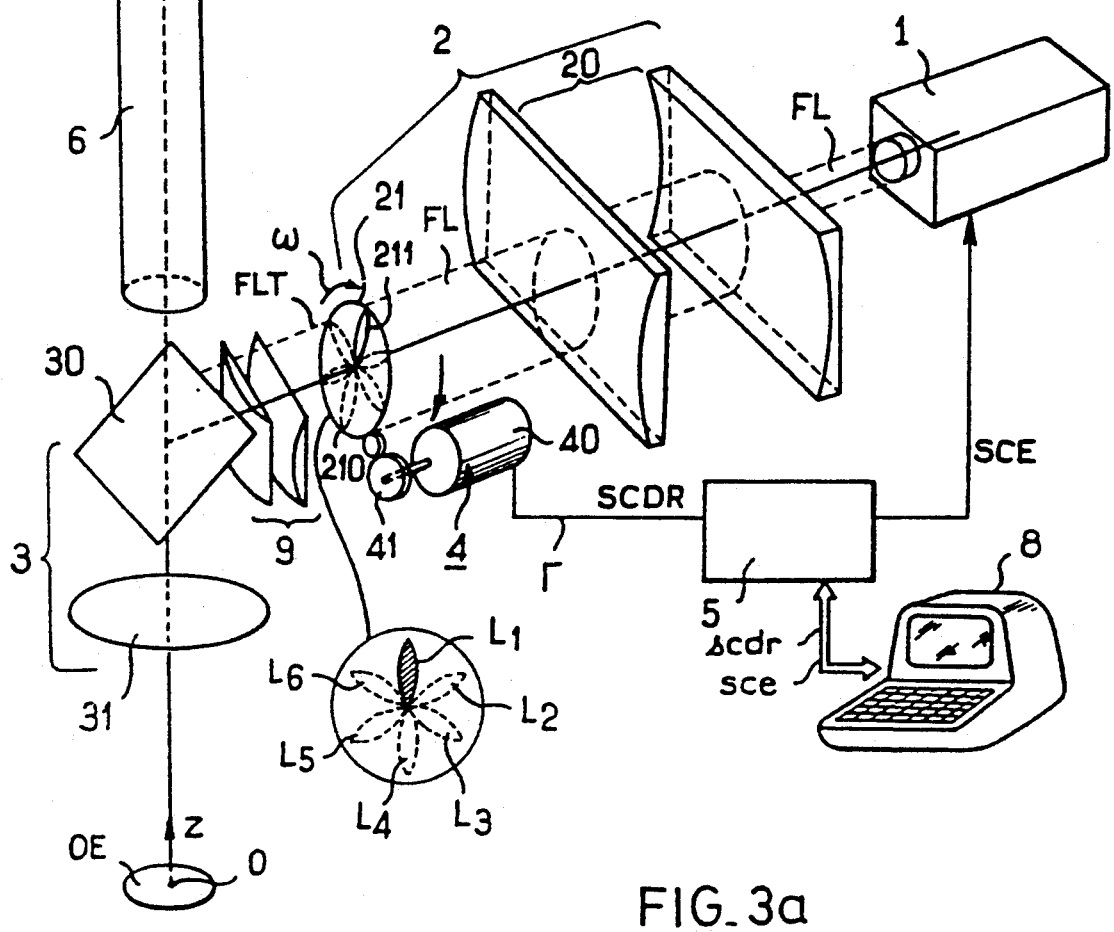

As further seen in FIG. 3a, the device in accordance with the invention comprises means 2 for generating a treatment laser beam denoted FLT comprising at least one lobe denoted L1 through L6 of elongate cross-section. In FIG. 3a the image of the treatment laser beam FLT has been shown to a larger scale, it being possible to show this image on a screen, for example, not shown in FIG. 3a.

The device in accordance with the invention also comprises means 3 for focussing the image of the lobe or lobes L1 through L6 of the treatment laser beam FLT on the area of the eye OE to be corrected on the cornea of the latter. Of course, the means 2 for generating the treatment laser beam FLT and the means 3 for focussing the image cause a loss of energy of the laser pulses of the laser beam FL, but the energy delivered to the cornea COR is in the order of 5 millijoules per pulse. The energy density on the image of the lobes of the laser beam generated by the means 3 for focussing the image of the aforementioned lobes is in the order of 200 millijoules/cm$^2$ as previously explained.

According to an advantageous aspect of the device in accordance with the invention, means 4 for moving the image of the lobe or lobes of the treatment laser beam FLT are provided for moving the aforementioned image over the area of the eye OE to be corrected.

Means 5 for synchronising the displacement of the image of the lobe or lobes of the treatment laser beam FLT over the area of the eye to be corrected are provided to ensure synchronisation with the pulses of the treatment laser beam.

Although the precise mechanism of the ablation process is still the subject of research, in some aspects it may be regarded as similar to a micro-explosion causing by photodecomposition a discrete elementary ablation by each laser pulse. The total correction or ablation resulting from implementation of the method in accordance with the invention is effected by summation of a plurality of elementary discrete ablations.

According to another advantageous characteristic of the device in accordance with the invention shown in FIG. 3a, the means 3 for focussing the image of the lobe or lobes L1 through L6 of the treatment laser beam FLT make it possible to focus the aforementioned image in such a way that the generatrix of an end of the lobe or lobes or the axis of longitudinal symmetry of the aforementioned lobe or lobes of the treatment laser beam are coincident with the optical axis OZ of the eye to be treated. Of course, as shown in FIG. 3a, the device in accordance with the invention may advantageously comprise an alignment device denoted 6 consisting, for example, of an auxiliary laser emission device such as a low-power helium-neon laser enabling the practitioner to carry out the appropriate adjustments of the focussing means 3 relative to the optical axis OZ of the eye OE of the patient.

According to another advantageous characteristic of the device in accordance with the invention, the means 4 for displacing the image of the lobe or lobes of the treatment laser beam over the area of the eye to be corrected make it possible to displace the image of the aforementioned lobes L1 through L6 in rotation about the previously mentioned end generatrix or the longitudinal axis of symmetry of the lobe or lobes of the treatment laser beam FLT.

According to an advantageous aspect of the device in accordance with the invention, the latter enables the aforementioned rotation by increments of the angle of rotation denoted Γ.

In one specific embodiment of the device in accordance with the invention shown in FIG. 3a, the means 2 for generating the treatment laser beam FLT may advantageously comprise a focussing optical system 20. The focussing optical system 20 may consist of a Galilean telescope producing from the laser emission means 1 a laser beam FL of regular (for example cylindrical) cross-section.

According to another particularly advantageous aspect of the device in accordance with the invention, the means 4 for displacing the image of the lobe or lobes of the treatment laser beam in rotation may comprise, as shown in FIG. 3a, a mask or diaphragm 21 incorporating an object slit denoted 211. Of course, the object slit 211 is of elongate shape and illuminated, for example in parallel light, by the laser beam FL. One end of the object slit 211 is disposed, for example, at the centre of the diaphragm 21 and generates the aforementioned end generatrix of the treatment laser beam FLT or the longitudinal axis of symmetry of the lobes L1 through L6 of the treatment laser beam FLT.

The object slit 211 and the image of this object slit are rotated by drive means 40, 41 for rotating the mask or diaphragm 21.

Of course, but not in any limiting way, the diaphragm 21 may be a circular shape diaphragm and the drive means for the diaphragm 21 advantageously comprise a toothed ring denoted 210 disposed at the periphery of the diaphragm and a stepper motor 40 the drive shaft of which is fitted with at least one toothed wheel 41 meshing with the toothed ring 210.

To focus the image of the lobe or lobes of the treatment laser beam FLT, the focussing means 3 advantageously comprise a semi-reflecting mirror 30 consisting of a prism or the like, for example, serving by total reflection to transmit the treatment laser beam FLT and the alignment beam delivered by the alignment means 6, together with a focussing lens 31 constituting the objective lens of the device. The combination of the semi-reflecting mirror 30 and the focussing lens 31 serves to form the image of the treatment laser beam FLT on the area of the cornea to be treated, of course.

In a conventional way, all of the device in accordance with the invention and in particular the means 2 for generating the treatment laser beam FLT and the laser emission means are mounted on an optical bench and the focussing means 3 are mounted on a barrel that can be oriented by the practitioner for correct aiming onto the area of the eye to be treated. The corresponding mountings for the aforementioned component parts as a whole will not be described as they constitute part of the prior art in the field of high-precision optical instruments.

A more detailed description of the diaphragm enabling operations as previously described herein by means of the image of the laser beam lobe moved in rotation over the area of the eye to be treated will now be given with reference to FIGS. 3b, 3c, 3d and 3e.

One embodiment of the object slit 211 of the diaphragm 21 will be described first in connection with treatment or operation by keratomileusis for myopia, the image of the lobe or lobes of the treatment laser beam FLT being rotated about the optical axis OZ of the eye to be treated.

Figure 3B:
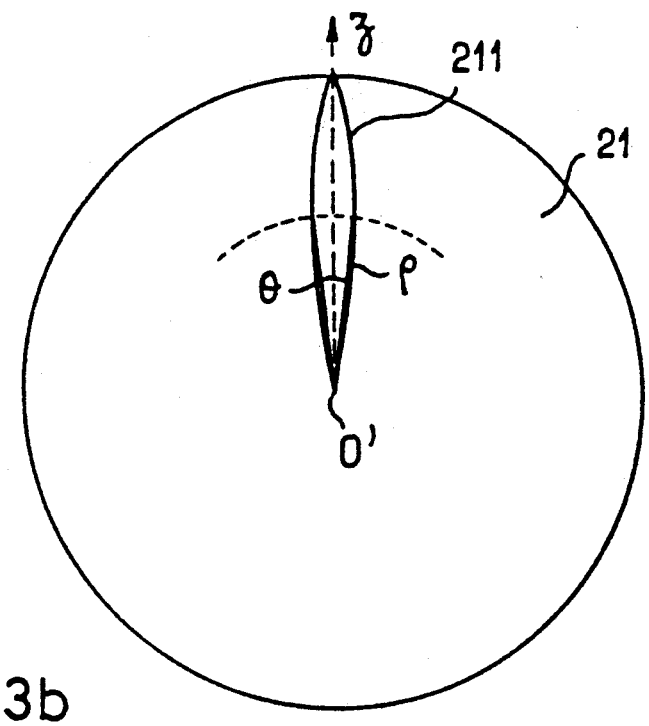

Referring to the aforementioned FIG. 3b, the object slit 211 of the diaphragm 21 has a profile satisfying the equation:

$$\theta(\rho) = \Gamma \frac{A_0}{a(e)}\left(1 - \frac{\rho^2}{R^2}\right) = \theta(0)\left(1 - \frac{\rho^2}{R^2}\right) \tag{9}$$

In the aforementioned equation, $\theta(\rho)$ represents the aperture angle of the slit defined as the angle at the centre of a circle with its centre at the end of the object slit, for generating the end generatrix or the axis of symmetry of the treatment laser beam FLT with for radius the corresponding value $\rho$ of the distance from a point on the edge of the slit or lip of the object slit or of the lobe of the laser beam to the aforementioned centre.

In FIG. 3b it will be noted that the object slit 211 has convex lips or edges, the aperture angle $\theta(0)$ of the slit at the origin, that is to say at the centre O' at the end of the slit being maximum.

$\Gamma$ represents the increment of angular rotation as previously mentioned. It will be noted that equation (9) represents the equation in polar coordinates of one of the lips of the slit, the other being deducible by considerations of symmetry.

Another example of an embodiment of an object slit 211 of the diaphragm 21 for treatment of hypermetropia by keratomileusis in the case where the operation is conducted by rotating the image of the lobe or lobes of the treatment laser beam FLT will also be described with reference to FIG. 3c.

In this case, as shown in the aforementioned figure, the profile of the slit 211 satisfies the equation:

$$\theta(\rho) = \Gamma \frac{A_0}{\bar{a}(e)} \frac{\rho^2}{R^2}, \rho \in [0, v], v < R \quad (10)$$

$$= \theta_{max} \frac{\rho^2}{R^2} \text{ wheren } \theta_{max} = \Gamma \frac{A_0}{\bar{a}(e)}$$

In equation (10) the parameters are given according to the definitions previously given. It will be noted that the lips of the slit 211 in the case of FIG. 3c are substantially concave up to a particular value of the radius $\rho$, this particular value being denoted $v$. It will be noted that the corresponding lip then has a point of inflection, the curvature of the latter becoming convex and decreasing regularly up to the end of the slit corresponding to the maximum longitudinal dimension of the latter. This continuous decrease in the aperture angle $\theta$ beyond the value of the radius $\rho = v$ advantageously serves to prevent excessive discontinuity at the periphery of the resulting total ablation. In a non-limiting way and by way of example only, the particular value of $v$ is substantially equal to $\frac{2}{3}$ of the maximum longitudinal dimension of the slit.

Of course, as shown in FIG. 3d in particular, the diaphragm 21 may advantageously comprise a plurality of elementary object slits denoted $211_1$, $211_i$ through $211_n$ in the aforementioned figure. Each elementary object slit generates a corresponding lobe of the treatment laser beam FLT, of course. The number of slits in the same diaphragm 21 is limited only by the maximum aperture $\theta_{max}$ of the object slit in question, the aperture angle at the origin $\theta(0)$ of each slit in the case of FIG. 3d and $\theta(R)$ in the case of FIG. 3c, for treatment of hypermetropia by keratomileusis.

It will be noted, of course, that increasing the number of object slits on the diaphragm provides for a commensurate decrease in the total operation time, since the summation of the successive elementary ablations achieved on the area to be treated by rotating the diaphragm and the object slit is added to the spatial summation due to the corresponding distribution of the various object slits on the diaphragm. It will be noted that in the case of multiple slits they may be regularly distributed over the diaphragm and all meet at their common end situated of the axis of rotation. Each of the slits generates in this way one lobe of the treatment laser beam FLT. In the case of slits used for treatment of myopia by keratomileusis, adjacent slits tangential to the centre have a su-face area exactly equal to one-half the surface area of the disk within which the slits are inscribed.

It will be noted that the choice of the angular rotation increment $\Gamma$ actually determines the surface area of the object slit or slits used and vice versa. The choice of the angular increment $\Gamma$ and the maximum aperture angle $\theta_{max}$ are governed by the following considerations:

A narrow slit corresponding to a small angular increment $\Gamma$ enables use of a small part of the laser beam FL with the possibility of choosing the most homogeneous part of the latter, use of a low-power laser and also irradiation of a small part of the cornea by each pulse. Furthermore, increasing the number ND of slit images that are totally separated or at worst tangential, the number of images ND being denoted $ND_1$ in the case of treatment of myopia by keratomileusis and $ND_2$ in the case of treatment of hypermetropia by keratomileusis, means that the sequence of positions of the irradiated slits can be programmed to minimise heating of the cornea.

On the other hand, too small a rotation increment $\Gamma$ can lengthen the correction or treatment period.

In practice it is more advantageous to have a limited set of slits and to vary the rotation increment $\Gamma$ as appropriate to the required correction.

Thus a slit is totally defined by:

its length which defines the radius of the corrected area, that is to say the parameter R defined by the practitioner, the type of correction or operation carried out, that is to say keratomileusis for myopia or hypermetropia, the maximum aperture angle $\theta_{max}$ appropriate to the type of correction or operation carried out.

For optimum performance of the operation, the device in accordance with the invention comprises means 8 for calculating the angular rotation increment $\Gamma$ which, for a given object slit (the slit having been chosen beforehand by the practitioner, of course) satisfies the equation:

$$\Gamma = \theta_{max} \frac{\bar{a}(e)}{A_0} \quad (11)$$

The calculation means 8 then used to determine the number of laser emission pulses NI, this number of laser pulses being denoted $NI_1$ in the case of treatment of myopia by keratomileusis. The number $NI_1$ of laser emission pulses satisfies the equation:

$$N_{I1} = \frac{2\pi}{\Gamma} = N_{D1} \frac{A_0}{\bar{a}(e)} \quad (12)$$

In the aforementioned equation $ND_1$ represents the number of separate or adjacent slit images that can be formed on the area of the cornea COR to be treated.

The calculation means 8 are also used to calculate the minimum total irradiation time denoted $T_{min}$ or $T_{1min}$ in the case treatment of myopia by keratomileusis. In this case, the minimum total irradiation time satisfies the equation:

$$T_{1min} = N_{I1} \frac{\tau(e)}{N_{D1}} = \tau(e) \frac{A_0}{\bar{a}(e)} \quad (13)$$

In this equation, $\tau(e)$ represents the minimum time interval between two successive irradiations of the same point on the cornea. The value of $\tau(e)$ is established experimentally and is the threshold beyond which heating of the cornea may occur. The value $T_{1min}$ depends of course on the energy flux but does not depend on the rotation increment $\Gamma$. This is because all of the $ND_1$ separate slits can be irradiated in the aforementioned interval $\tau(e)$. In practice, the type of laser used to produce the laser pulses and the maximum speed of displacement of the slit may limit the frequency at which the pulses can be delivered.

The refractive eye surgery device using laser illumination in accordance with the invention may also be used to correct astigmatism of the cornea COR or of the eyeball.

In a case like this the ablation profile varies with the meridian in question of the eyeball, this meridian consisting of the intersection with the surface of the cornea of a plane containing the optical axis OZ of the eyeball oriented at an angle $\beta$ in azimuth relative to a plane containing the previously defined reference direction OX. In the case where, as previously defined, the reference directions OX and OY correspond to the principal directions of astigmatism, and in the case of myopic astigmatism, the ablation function satisfies the equation:

$$A(h,\beta) = A_0(\beta)\left(1 - \frac{h^2}{R^2}\right) \quad (14)$$

In this equation, $A_0(\beta)$ is equal to:

$$A_0(\beta) = \frac{1}{2} R^2 \left(\frac{1}{r(\beta)} - \frac{1}{r}\right) \quad (15)$$

$$r(\beta) = r_x \cos\beta + r_y \sin\beta$$

From the equations (6), (7) and (8) previously given in this description, it is possible to compensate for the variations in $A_0(\beta)$ by varying the rotation increment $\Gamma$ as a function of $\beta$.

In this way it is possible to correct astigmatism of the eyeball with slits identical to those previously described with reference to FIGS. 3a, 3b, 3c, 3d by modulating the angular rotation increment $\Gamma$ as a function of the angle $\beta$ defining the meridian of the cornea of the eyeball.

To this end, the device in accordance with the invention comprises means for modulating the angular rotation increment $\Gamma$ as a function of the angle $\beta$, this angle rotation increment $\Gamma$ as a function of the angle $\beta$ satisfying the equation:

$$(\beta) = \theta_{max} \frac{\bar{a}(e)}{A_0(\beta)} \quad (16)$$

In this equation, $A_0(\beta)$ represents the ablation at the origin near the optical axis OZ of the eyeball in the direction with azimuth angle $\beta$.

However, in the case of myopic astigmatism, the ablation at the centre is not constant and varies with the meridian. To establish circular symmetry of the cornea the device in accordance with the invention may comprise as shown in FIG. 3e at least one auxiliary diaphragm 21 provided with an object slit 211 of circular sector shape the equation for which in polar coordinates is $\theta(\rho)=k$ where k is a constant. The aforementioned auxiliary slit 211 enables such correction by means of supplementary irradiation and rotational displacement by the rotation increment $\Gamma(\beta)$ modulated as a function of the azimuth angle $\beta$ to establish a constant ablation at the origin 0 without modifying the radius of curvature of the cornea, however. The residual ablation to be effected during such supplementary irradiation using the slit 211 shown in FIG. 3e satisfies the equation:

$$\delta A(\beta) = A_0(0) - A_0(\beta)$$
with
$$A_0(0) = \frac{R^2}{2}\left(\frac{1}{\min(rx,ry)} - \frac{1}{r}\right)$$

in which equation min (rx,ry) represents the smaller of the values rx and ry.

The residual ablation effected during the supplementary irradiation is then obtained by modulating the angular rotation increment $\Gamma$ as a function of the azimuth angle $\beta$, the rotation increment $\Gamma$ satisfying the equation:

$$\Gamma(\beta) = \theta(0) \frac{\bar{a}(e)}{\delta A(\beta)} \quad (18)$$

It should be noted that this method introduces a discontinuity at the periphery of the resulting total ablation, this discontinuity being null for $\beta=0$, that is in the OX direction, and maximal for $\beta=\pi/2$, that is in the OY direction. The maximal value of this discontinuity is equal to:

$$\frac{R^2}{2}\left(\frac{1}{ry} - \frac{1}{rx}\right) \quad (19)$$

with $rx < ry$.

This discontinuity can be resolved, as will be explained later in this description.

In an alternative embodiment of the device shown in FIG. 3a, for the purpose of compensating by correction astigmatism of the eyeball and of the cornea, the device may comprise upstream of the focussing means 3, on the path of the treatment laser beam FLT, an anamorphic optical system 9 in which the magnification depends on the azimuth angle $\beta$. In this case, the iso-ablation curves on the cornea are ellipses. Correction of astigmatism implies that the total resulting ablation as a function of the azimuth angle $\beta$ is not constant. Anamorphic systems are systems in which the magnification depends on the aforementioned azimuth angle $\beta$. Generally speaking, and with the orientation of the axes OX and OY previously defined relative to the eyeball in FIG. 2a, an anamorphic system having a corresponding magnification denoted $M_x$ and $M_y$ at an elementary surface dS of the object, that is to say of the object slit 211, corresponds to an elementary surface $dS' = M_x \cdot M_y \cdot dS'$ of the image given by the anamorphic system. Under these conditions, the image of a circle obtained by means of the rotating slit or by some other equivalent means is an ellipse. Thus the iso-energy curves in the object plane of the anamorphic system, that is to say of the object slit 211, are circles and the images of these circles given by the anamorphic system are ellipses. Given that the total resulting ablation at a given point on the cornea is proportional to the energy received at that point, the iso-ablation curves are consequently ellipses. $R_x$ and $R_y$ being the half major axes of these ellipses, the magnifications $M_x$ and $M_y$ of the anamorphic system 9 must be in the same ratio as the aforementioned half major axes. The anamorphic system 9 may consequently comprise two cylindrical lenses the longitudinal axes of which are orthogonal and respectively oriented to define the corresponding directions OX and OY, the lenses having respective magnifications $M_x$ and $M_y$. These anamorphic optical systems as such are prior art and because of this they will not be described in more detail in this description.

Of course, to facilitate the work of the practitioner the device in accordance with the invention may be provided with an auxiliary diaphragm 21 having an object slit 211 of circular arc shape with a particular radius of curvature. This type of object slit is shown in FIG. 3f by way of non-limiting example. It is used to make circular incisions for arc-shaped corneal grafts, for example.

Also, the object slit as shown in FIG. 3e may also be used to correct astigmatism as previously described by modulating the rotation increment as a function of the azimuth angle $\beta$, to carry out such operations as removal of a locally parallel faced meniscus for epikeratothakia, or removal of a parallel surface corneal disc from a donor or removal of a surface to be modified by the laser for correcting myopia or hypermetropia, with a view to carrying out lamellar grafting. The lamellar grafting operations may then be carried out with constant rotation increments $\Gamma$, the ablation obtained during this operation corresponding to that of a locally parallel faced meniscus the edges of which are substantially rectilinear.

An alternative embodiment of the device in accordance with the invention more particularly adapted to operations such as those previously described will be described with reference to FIG. 4a.

In the embodiment shown in the aforementioned figure, but in a non-limiting way, the means 4 for displacing the image of the lobe or lobes of the treatment laser beam FLT over the area of the line to be treated provide for displacement in translation in a direction d substantially perpendicular to the largest dimension denoted Oz of the lobe of the treatment laser beam FLT. In this case, as will be described in more detail later in this description, the treatment laser beam FLT may advantageously comprise two lobes or component parts of a single lobe symmetrical relative to a centre of symmetry denoted O''.

Figure 4A:
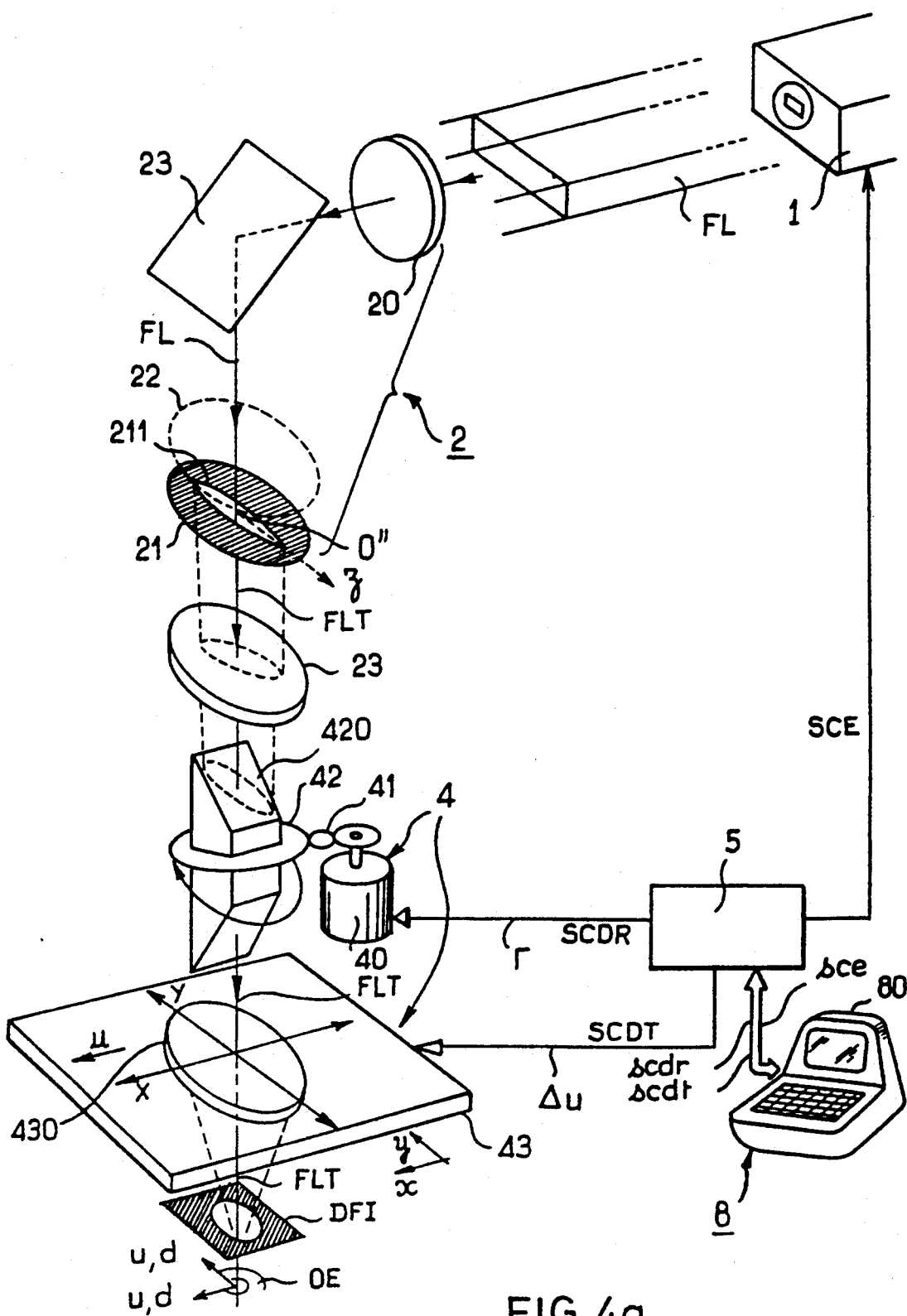

According to an advantageous characteristic of the device in accordance with the invention shown in FIG. 4a, the displacement in translation is advantageously effected by means of displacement increments denoted $\Delta u$. The displacement in translation is defined relative to the two reference directions OX, OY with $u=X$ or $u=Y$, these directions defining a plane tangential to the cornea at the point O on the optical axis of the eyeball as defined previously in FIG. 2a.

The means 4 for displacement in translation of the image of the lobe or lobes of the treatment laser beam FLT advantageously provide for displacement in translation of the latter in the orthogonal directions OX and OY.

As shown by way of non-limiting example in FIG. 4a, the means 4 for displacing the image of the lobe or lobes of the treatment laser beam FLT in translation may comprise in succession along the path of the laser beam FL: a fixed diaphragm denoted 21 comprising at least one object slit 211 of elongate shape. This object slit is illuminated with parallel light. As shown in a non-limiting way in FIG. 4a, the laser beam FL may be generated by the means 1 previously described in relation to FIG. 3a, the laser beam FL possibly having a rectangular cross-section obtained in the classical way by passing the emitted laser beam through suitable diaphragms. Of course, as shown in FIG. 4a, a lens 20, a direction-changing mirror 21 such as a semi-reflecting mirror enabling under conditions analogous to those of FIG. 3a transmission of an auxiliary alignment laser beam not shown in this figure and a field lens 22 are used to conduct the parallel light laser beam FL to the slit 211 in the diaphragm 21.

Moreover, as also shown in FIG. 4a, a first lens 23 is placed relative to the object slit 211 and to the diaphragm 21 so that the object slit 211 is in the object focal plane of the lens 23 to generate the lobe or lobes of the beam imaging the object slit in parallel light.

A rotating prism 420 is provided whereby rotation of the prism in question through an angle $\alpha$ rotates the emergent light beam, i.e. the treatment laser beam FLT, through an angle $2\alpha$.

Also, a second focussing lens 430 serving as an objective lens is movable in translation in the previously mentioned directions OX and OY.

It will be understood that the embodiment of the device in accordance with the invention shown in FIG. 4a is particularly advantageous in that it enables two methods to be used: in the first the treatment laser beam FLT is scanned in rotation, the focussing lens 430 being held in a fixed position and centred on the optical axis OZ of the eye, of course, the prism 420 then being rotated to obtain the corresponding scanning of the treatment laser beam; in the second method, with the prism 420 fixed in position, the treatment laser beam emerging from the prism 420 is directed along the optical axis OZ of the eye and the focussing lens 430 produces corresponding movement in translation of the treatment laser beam FLT by corresponding defocussing due to movement of the lens 430 in translation in direction X or in direction Y.

The rotator prism 420 may advantageously be a Dove or Wollastom prism. Also, a diaphragm denoted DFI may be provided between the lens 430 and the eye of the patient to limit the luminous intensity received by the eye OE of the patient. It may be disposed in the vicinity of or on the eye. Of course, other direction-changing mirrors can be provided on the path of the laser beam FL to obtain an appropriate optical path to enable unrestricted circulation of persons in the environment of the apparatus and the practitioner.

The device in accordance with the invention in FIG. 4a is particularly advantageous in that, over and above any possible operation by scanning the area of the eye to be treated in rotation, it also makes it possible to carry out this operation by scanning the laser beam over the area of the eye to be treated in translation, in particular in the previously mentioned two directions OX and OY. The lobe or lobes of the laser beam and the beam direction Oz being oriented in the OY direction, the scanning in one direction (the OX direction, for example) is obtained by means of the rotator prism 420. This orients the aforementioned direction Oz with the OX direction for subsequent movement of the treatment laser beam FLT in the direction perpendicular to the new orientation of the Oz axis, i.e. the direction OY. The displacement in translation is effected by displacing the lens 430 in the corresponding directions.

A more detailed description of an object slit 211 profile specifically used in the case where displacement in translation of the image of the object slit 211 is brought about to carry out the treatment or operation as aforementioned will be given with reference to FIGS. 4b, 4c, 4d.

Referring to FIG. 4b, the object slit 211 of the diaphragm 21 and consequently the image of the lobe or lobes of the treatment laser beam FLT for treatment and correction by keratomileusis of myopia and astigmatism has a substantially parabolic profile. The profile defined by one lip of the slit satisfies the equation:

$$E(z) = 2 E_{max} \left( \frac{1}{2} - \frac{z^2}{R^2} \right) \quad (20)$$

It will be noted for convenience that the slit 211 has a longitudinal axis denoted $O''x$.

In the above equation, the various parameters are defined as follows:

$E(z)$ represents the transverse dimension of the object slit or of the lobe of the treatment laser beam at the abscissa z on the longitudinal reference axis oriented relative to the slit. The abscissa is referenced relative to an origin point $O''$.

$E_{max}$ represents the maximal transverse dimension of the object slit 211.

While carrying out the aforementioned operation, the practitioner is required to displace the image of the object slit 211 in translation along a direction at least perpendicular to the longitudinal axis $O''z$ of the object slit 211. Of course, the image of the object slit 211 is then oriented in such a way that the longitudinal axis $O''z$ of the latter is oriented in one of the directions OX or OY of FIG. 2a. Thus for a direction u of orientation of the slit 211 or of its longitudinal axis $O''z$ in the direction OX or OY, the equation relating the aperture of the slit E(u) and the translation displacement increment denoted $\Delta u$, this displacement being in the direction perpendicular to the orientation direction u of the slit, is of the form:

$$E(u) = \Delta u \frac{A_0}{\bar{a}(e)} \left( \frac{1}{2} - \frac{u^2}{R^2} \right) \quad (21)$$

In this equation:

u represents the abscissa or position of the edge of the slit on the longitudinal axis of reference $O''z$, the slit itself being oriented n the direction u corresponds to the direction OX or to the direction OY, $\Delta u$ represents the translation displacement increment in the direction orthogonal to the aforementioned alignment direction i.e. in the direction OY or in the direction OX, $A^u{}_0$ represents the thickness of ablation or correction at the centre of the area of the cornea to be corrected at the time of displacement in translation of the object slit 211 or of the lobe of the treatment laser beam in the direction OY or in the direction OZ.

A description of an object slit 211 for treatment and correction of the cornea by keratomileusis for hypermetropia and hypermetropic astigmatism will also be given with reference to FIG. 4c.

In the case of the aforementioned operation, the object slit 211 and the corresponding lobe or lobes of the treatment laser beam FLT have a substantially parabolic profile satisfying the equation:

$$E(z) = E_{max} \left( \frac{z^2}{R^2} \right) \quad (22)$$

As in FIG. 4b the orientation of the longitudinal axis $O''z$ of the object slit 211 in the direction OX or in the direction OY serves to establish the relationship defining the connection between the displacement increment $\Delta u$ in the direction perpendicular to the orientation direction and the aperture E(u) of the slit 211, this relationship being of the form:

$$E(u) = \Delta u \frac{A^u{}_0}{\bar{a}(e)} \left( \frac{u^2}{R^2} \right) \quad (23)$$

In the above equations (22) and (23), the same notation designates the same parameters as in the previous equations (20) and (21).

In an analagous manner to an operation carried out by scanning the image of the object slit 211 in rotation, in the case of scanning the translation the values of the displacement increment in the direction perpendicular to the alignment direction of the axis $O''z$ of the object slit 211 and the irradiation times satisfy similar equations.

Consequently, in the FIG. 4a embodiment, the device in accordance with the invention comprises calculation means denoted 8 for calculating the translation displacement increment $\Delta u$ in the direction OY or OX for an orientation u in the direction OX, OY, the increment for a given object slit satisfying the equation:

$$\Delta u = E_{max} \frac{\bar{a}(e)}{A^u{}_0} \quad (24)$$

In this equation the parameters $\bar{a}(e)$ and $A^u{}_0$ correspond of course to the definitions given previously in this description.

Also, in the embodiment shown in FIG. 4a, the device in accordance with the invention also comprises means 8 for calculating the number of laser emission pulses denoted $NI_2$ and the number of translation displacements increments $\Delta u$ in the direction OY, OX. The number $NI_2$ of pulses satisfies the equation:

$$NI_2 = \frac{2\pi}{\Delta u} = ND_2 \frac{A^u{}_0}{\bar{a}(e)} \quad (25)$$

In this equation $ND_2$ represents the number of totally separate or adjacent images that can be formed on the cornea.

In the same way as in the case of treatment or correction by an object slit or object slit image performing a rotating scan, in the FIG. 4a embodiment the calculation means 8 may also be used to calculate the minimum total radiation time denoted $T_{2min}$. This satisfies the equation:

$$T_{2min} = Nl_2 \frac{\tau(e)}{ND_2} = \tau(e) \frac{A''_0}{a(e)} \quad (26)$$

In this equation, $\tau(e)$ represents the minimum time interval between two successive irradiations of the same point on the cornea.

As will be noted from FIGS. 3b, 3c, 3d, 3e, 4b, 4c and 4d in particular, the object slits 211, whether used during an operation to effect scanning in rotation or in translation of the area of the cornea to be treated, are symmetrical with respect to their longitudinal axis O'z or O"z. This corresponds to a particularly advantageous, non-limiting embodiment in which, without departing from the scope of the present invention, the slits may be asymmetrical with respect to the longitudinal axis O'z or O"z provided that the corresponding width of the slit at a given point z is substantially the same.

As will be noted in FIG. 4c, in the case of an object slit 211 used for treatment of hypermetropia by scanning in translation the object slits, whether they generate one or more lobes of the treatment laser beam FLT scanned in rotation or in translation, may advantageously comprise a curvilinear shape edge denoted C at the end. This edge at the end is, as shown to a larger scale in FIG. 4c, symmetrical with respect to the longitudinal axis O"z. The curvilinear shape departs from the variation law $\rho =$ constant, representing a circular arc in polar coordinates, to eliminate edge effects from the resulting profile of the total ablation obtained.

As will be noted in FIG. 4c, in a non-limiting way, the curvilinear shape C may be concave and convex with a point of inflection. Likewise, provided that the curvilinear shape C departs from the variation law $\rho =$ constant, the edge at the end may equally well be continuously concave, as shown in dashed outline in the enlarged view of FIG. 4c.

A curvilinear character of this kind for the edge of the slits at the end improves the continuity of the curvature in transitions between corrected and uncorrected areas. Thus any slit of which an edge at the end has a non-zero width or aperture could comprise the aforementioned curvilinear slit C. The curvilinear shape C, in the absence of any point of inflection, provides for transitions between corrected and uncorrected areas at which there is a discontinuity in the curvature.

Of course, in an analagous way to the embodiment of the object slits in FIG. 3e in the case of rotational scanning for a plurality of object slits 211 on the same diaphragm 21, in the case of treatment by scanning in translation it is also possible to use a plurality of object slits 211 on the same diaphragm. A diaphragm of this kind is shown in FIG. 4d, in which three slits $211_1$, $211_2$ and $211_3$ have been shown by way of non-limiting example. The various object slits are spaced in a direction perpendicular to their longitudinal axis O"z by a distance at least equal to the widest aperture $E_{max}$ thereof.

A prototype of the device in accordance with the invention was manufactured with the object slits 211 as described previously with reference to FIGS. 3b, 3c, 3d, 4b, 4c and 4d.

To give a non-limiting example, in the case of an object slit such as that shown in FIG. 3b, the object slit 211 had a length substantially equal to 3.2 mm, its length being measured along the longitudinal axis O'z, and a width or maximal dimension in the direction perpendicular to the aforementioned longitudinal axis substantially equal to 0.8 mm.

Figure 3C:
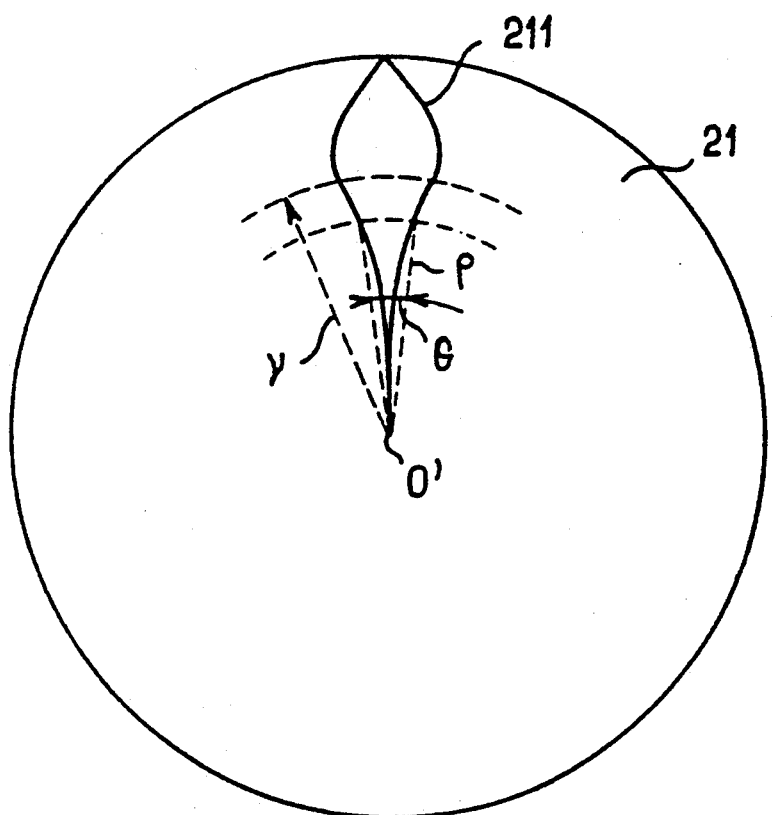

An object slit 211 as shown in FIG. 3c had a length substantially equal to 3.2 mm and a maximal width in the order of 1.4 mm.

In the case of an object slit 211 as shown in FIG. 4b the length of the slit along the longitudinal axis O"z was in the order of 6 mm and its maximal width in the order of 1 mm.

Of course, the foregoing dimensions of the object slits 211 are given by way of non-limiting example only, since it is to be understood that these dimensions vary according to the total magnification of the optical system of the device in accordance with the invention. The latter may of course and advantageously be provided with an optical system offering variable magnification so that from a particular design of object slit the practitioner is in a position to choose the final dimension of the image of the lobe or lobes of the treatment laser beam FLT given by the aforementioned object slits.

In accordance with another advantageous characteristic of the device in accordance with the invention, with particular reference to the FIG. 4a embodiment in which the diaphragm 21 is fixed, each slit may advantageously have a variable profile to provide for compensation for any irregular distribution of the light energy over the cross-section of a lobe of the treatment laser beam FLT.

Figure 4D:
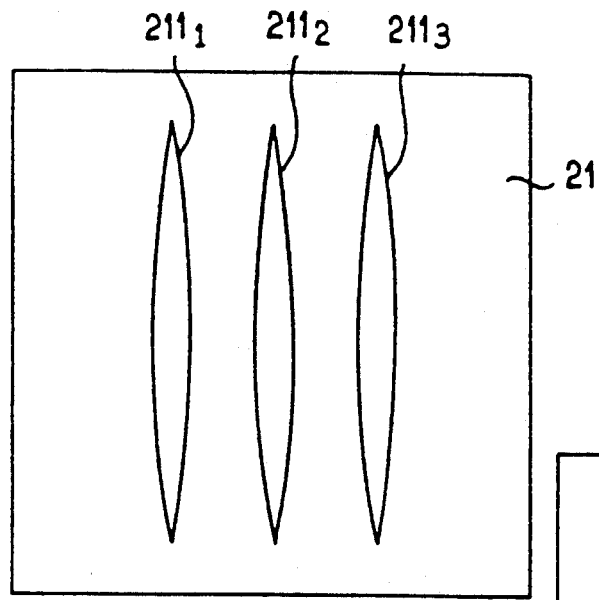
Figure 4E:
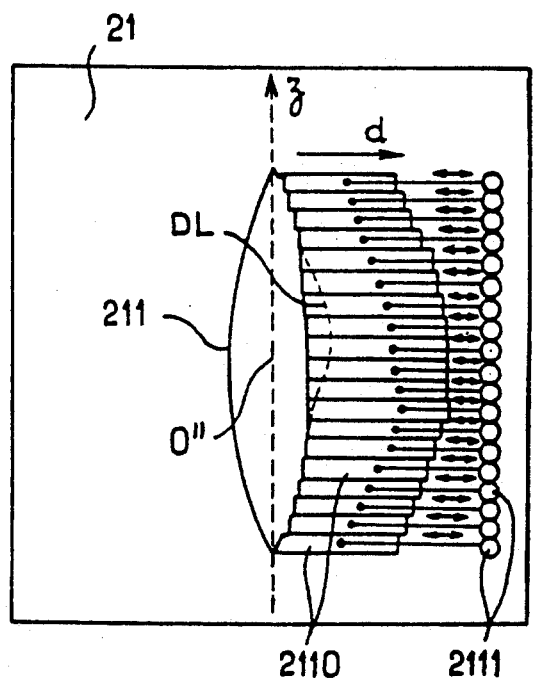

As will be noted in FIG. 4e, the variable slit 211 may comprise at least one edge made up of mobile strips denoted 2110, these strips being movable in translation in a direction perpendicular to the longitudinal axis O"z of the slit. The mobile strips 2110 may of course be disposed to slide relative to each other, each being adapted to be driven by the intermediary of a motor or like means 2111. It will be understood of course that in the case of the FIG. 4e embodiment the dimensions of the object slit 211 may be increased to facilitate implementation of the movable strips, the magnification of the optical system of the device in accordance with the invention being adjusted accordingly.

One example of an operation for treatment of myopic astigmatism by keratomileusis using the device in accordance with the invention shown in FIG. 4a and scanning of the area to be treated in translation will now be described with reference to FIG. 5a.

The total resulting ablation is in this instance obtained by means of a slit such as that shown in FIG. 4d, for example, the image of the slit or the lobe of the treatment laser beam FLT being displaced in a direction perpendicular to the longitudinal axis O"z in consecutive elementary increments. The elementary displacement increments being equal, the effect of the treatment is to produce a channel of uniform parabolic profile. The length of the channel is of course equal to the distance over which the slit is displaced and its width is equal to the length of the slit.

In a particularly advantageous method of working, two operations are effected along two perpendicular axes to achieve complete correction of the cornea COR.

In the case of myopia, this method of working has the following advantages:

it eliminates the problem of precisely focussing the end or the image of the slit on the rotation axis in the case of scanning in rotation, and it enables all types of astigmatism to be corrected.

The longitudinal axis O"z of the slit being oriented in the direction OX, for example, in FIG. 2a, irradiation of the object slit 211 in successive positions spaced by a constant translation increment ΔY in the direction OY in FIG. 2a within a range of displacement ranging between $-R/\sqrt{2}$ and $+R/\sqrt{2}$ serves to obtain with respect to the axis OX an ablation profile B(X) defined by the equation:

$$B(X) = \bar{a}(e) \left[ \frac{E(X)}{\Delta^x_y} \right] , \sqrt{X} \epsilon \left[ \frac{-R}{\sqrt{2}} , \frac{R}{\sqrt{2}} \right] \quad (27)$$

In this equation:

E(X) represents, of course, the profile of the slit at the abscissa X and $\Delta^x_y$ represents the constant translation displacement increment in the direction Y, the slit being oriented in the direction X, R is the radius of the area to be corrected centered at O".

As previously mentioned in this description, when the axes OX and OY from FIG. 2a correspond to the principal directions of the meridians corresponding to the ends of the curves at the centre of the cornea, the principal astigmatism directions, the ablation profile to be obtained is expressed by the equation:

$$A(X,Y) = A^x_0 \left( \frac{1}{2} - \frac{X^2}{R^2} \right) + A^y_0 \left( \frac{1}{2} - \frac{Y^2}{R^2} \right) \quad (28)$$

In equation (28) the parameters $A^x_0$ and $A^y_0$ satisfies the equations:

$$A^x_0 = \frac{R^2}{2} \left( \frac{1}{r_x} - \frac{1}{r} \right) \quad (29)$$

$$A^y_0 = \frac{R^2}{2} \left( \frac{1}{r_y} - \frac{1}{r} \right) \quad (30)$$

The ablation function may be regarded as the result of summing two ablation functions, one a function of X only and the other a function of Y only. In equations (29) and (30), $r_x$ represents the radius of curvature of the cornea in the direction OX and $r_y$ represents the radius of curvature in the direction OY, $r$ representing the radius of curvature of the cornea in a meridian direction at the azimuth angle β previously mentioned.

Adopting the following notation:

$$A_0 = \frac{A^x_0 + A^y_0}{2} \quad (31)$$

$$R_x = R \sqrt{\frac{A_0}{A^x_0}} \quad (32)$$

$$R_y = R \sqrt{\frac{A_0}{A^y_0}} \quad (33)$$

the equation for the resulting total ablation function may be written:

$$A(X,Y) = A_0 \left( 1 - \frac{X^2}{R^2_x} - \frac{Y^2}{R^2_y} \right) \quad (34)$$

The iso-ablation curves are therefore ellipses in the general case and the equation for the ellipse which delimits the ablation contour is:

$$\frac{X^2}{R^2_x} + \frac{Y^2}{R^2_y} = 1 \quad (35)$$

Figure 5A:
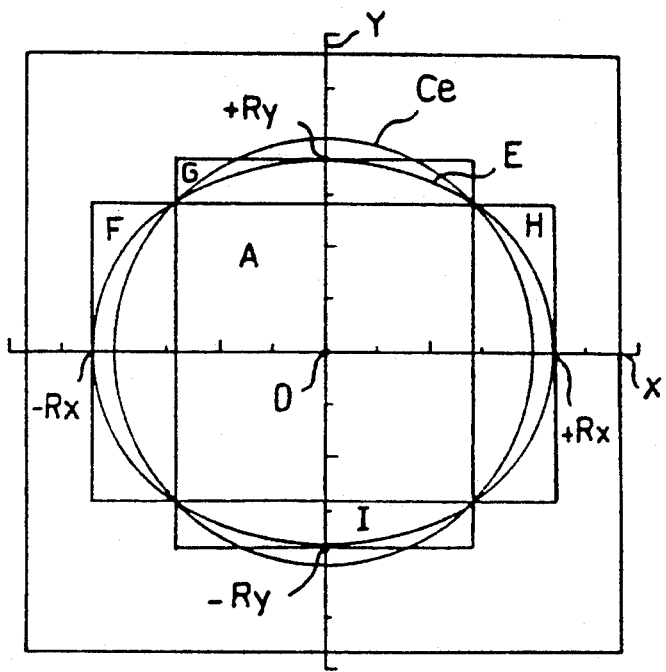

As shown in FIG. 5a, theory indicates that the resultant ablation should extend from $-R_X$ to $+R_X$ on the OX axis and from $-R_Y$ to $+R_Y$ on the OY axis. The ablation profile is thus contained within two orthogonal rectangles with respective lengths $2R_X$ and $2R_Y$ and the same width $R\sqrt{2}$ whose common area is a square inscribed in the circle Ce of radius R centered at O. The ablation profile obtained is perfect within the square where they intersect although a satisfactory approximation of the ablation profile is nevertheless obtained outside the square in the areas peripheral to the latter, the areas FGHI in FIG. 5a, the central area consisting of the square being denoted A.

In the case of pure myopia with no astigmatism, $r_x = r_y$ and $A_0 = A^x_0 = A^y_0$.

Thus correction or treatment by means of an object slit scanned in translation along two orthogonal directions produces an optimal effect where the areas scanned by the treatment laser beam FLT in the aforementioned directions intersect, that is over a square in plane projection.

To extend this action beyond the intersection square and to obtain satisfactory correction over a substantially circular area it is possible to extend the lateral scanning of the treatment laser beam FLT while modulating the displacement increment Δu between two adjacent positions, the aforementioned increment Δu remaining constant in the intersection area, of course.

It has been shown that the ablation profile in the first area made up of the three areas A, F and H (that is for $-R/\sqrt{2} \leq X \leq +R/\sqrt{2}$) is achieved by irradiating a slit parallel to the axis OX and moving by increments $\Delta^Y_X$ in the direction perpendicular to the OY axis.

Likewise, the ablation profile in the area made up of the areas I, A and G (that is for $-R/\sqrt{2} \leq Y \leq R/\sqrt{2}$) is achieved by irradiating a slit parallel to the OY axis moved in increments $\Delta^Y_X$ or Δu along the OX axis.

This second operation, correction of the profile along OY, does not modify the profile along an axis parallel to OX, but deepens it uniformly (Y = constant) in particular by an amount $A^y_0$ over all of the axis OX, that is for Y = 0.

To complete the resulting total ablation profile along OX and to avoid any discontinuity for $X = \pm R/\sqrt{2}$ the scanning in translation along OX of the slit which generates the ablation profile along OY can be extended beyond these values, with the translation displacement increment along OX increasing with X for $|X| > R/\sqrt{2}$.

The device in accordance with the invention as shown in FIG. 4a uses the calculation means 8 to determine the value of the linear displacement increment denoted $\Delta^Y_X$, for example to obtain an exact extension of the parabolic profile for Y = 0, the translation displacement increment for a corresponding ablation function satisfying the equation:

$$A(X,0) = A_0 \left(1 - \frac{X^2}{R^2_x}\right) \quad (36)$$

The translation displacement increment then satisfies over all of the treatment domain comprising areas F, A and H in FIG. 5a the equation:

$$\Delta^y_x(X) = \begin{bmatrix} E_{max} \dfrac{\bar{a}(e)}{A_0\left(1 - \dfrac{X^2}{R_x^2}\right)}, \text{ for } \dfrac{R}{\sqrt{2}} \leq |X| \leq R_x \\ E_{max} \dfrac{2\,\bar{a}(e)}{A_0^y}, \text{ for } |X| < \dfrac{R}{\sqrt{2}} \end{bmatrix} \quad (37)$$

In equations (36) and (37), $R_X$ defines the total irradiation domain in the X direction.

The resulting total ablation function $A_X(X,Y)$ which defines the resulting total ablation in rectangles F and H in FIG. 5a, that is to say for $$\frac{R}{\sqrt{2}} \leq |X| \leq R_X, |Y| \leq \frac{R}{\sqrt{2}},$$

satisfies the equation:

$$A_x(X,Y) = \frac{E(Y)}{\Delta^Y_X} \bar{a}(e) \quad (38)$$

In this equation E(Y) represents, of course, the profile of the slit used, the slit having its longitudinal axis O″z oriented in the Y direction and $\Delta^Y_X$ corresponding to the values of equation (37) for the values of X included in the areas F and H.

The working method previously described with a slit procuring scanning of the treatment laser beam FLT in translation or using a slit with a parabolic profile as explained previously in this description thus yields an ablation profile which over the periphery of the area of an ellipse denoted E in FIG. 5a, with half-axes $R_x$ and $R_y$, contains eight "perfect" points by which is meant points of zero ablation.

Of course, in the case where there is a requirement not to irradiate the cornea COR beyond an area of radius R it is possible to mask the latter with a mask comprising a circular hole of radius R.

Figure 5B:
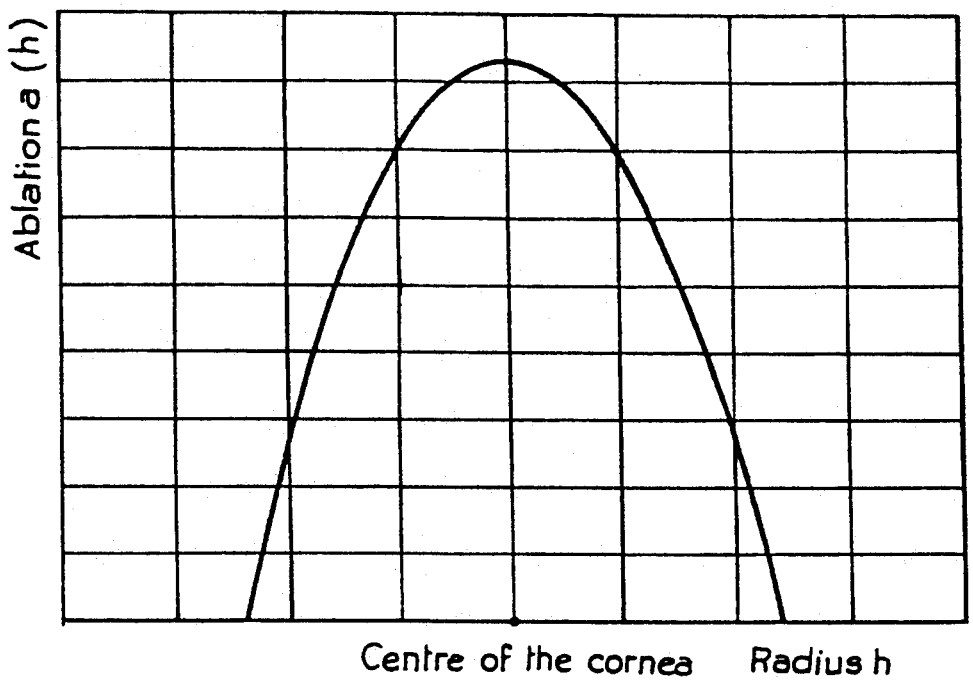
Figure 5C:
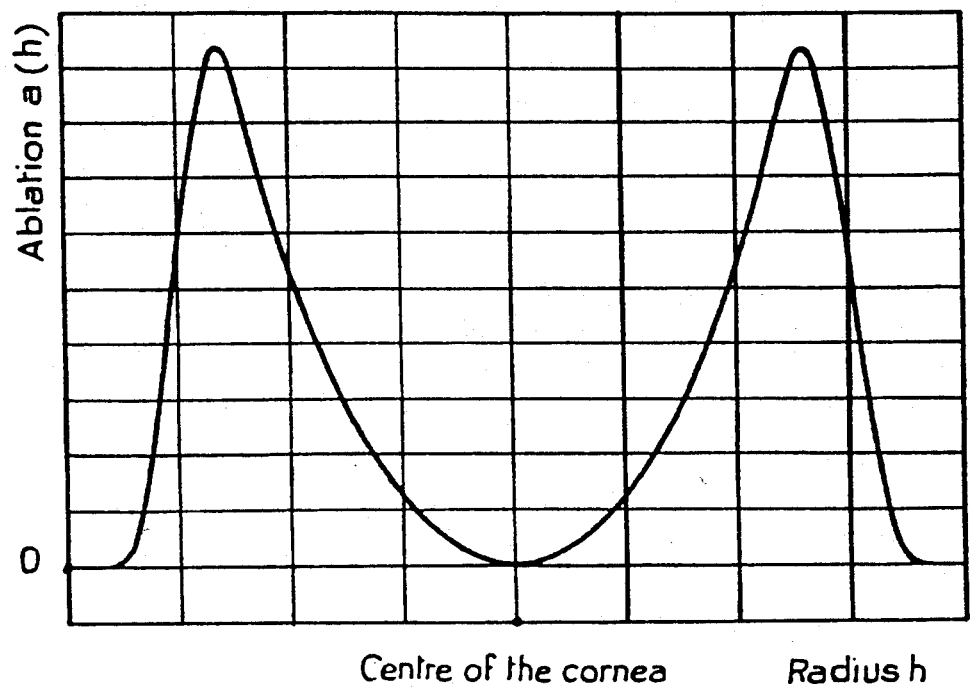

There are shown in FIGS. 5b and 5c respectively a profile characteristic of keratomileusis ablation for myopia with no astigmatism and a profile characteristic of keratomileusis ablation for hypermetropia.

In FIGS. 5b and 5c the units have not been marked on the coordinate axes. In the case of an operation by keratomileusis on myopia, an ablation corresponding to a correction of 15 diopters has a depth of 0.15 mm and extends over an area 5 mm in diameter. The initial radius of curvature is increased to 10.6 mm.

In the case of FIG. 5c, in which the units have not been shown on the coordinate axes, an ablation corresponding to a correction of 15 diopters has a depth of 0.15 mm and extends over an area 9 mm in diameter. The initial radius of curvature of 7.8 mm is reduced to 5 mm.

The device in accordance with the invention makes it possible to overcome the limitations of prior art devices through the use of an illumination and treatment laser beam the specific shape and displacement of which are computed so that their combination produces the required ablation shape.

When the slit or slits is or are irradiated by a particular pulse from the laser the image of the slit(s) projected onto the cornea COR is, so to speak, etched on to the surface and causes by photodecomposition the elementary ablation in question. The sum of these elementary ablations distributed over the cornea in accordance with the mathematical laws previously established produces the required modification to the shape of the cornea.

Unlike the prior art devices, in which the concepts of illumination time were involved, the concepts of the laser pulse frequency and of the speed of displacement of the object slit (or its image) are replaced by the concepts of linear or angular increments, as appropriate, between two adjacent positions of the image or of the lobe of the treatment laser beam. Here "adjacent" is to be understood in the geometrical rather the temporal sense. In other words, the fact that two geometrically adjacent, that is to say geometrically consecutive, elementary ablations are temporally consecutive is not relevant. Generally speaking, they are not.

All the considerations previously mentioned combined with the concept of a threshold relating to each elementary ablation serves through summation of the elementary ablations in question to obtain a corrected or treated surface that is particularly satisfactory and the degree of roughness of which is substantially less than 1 μm.

In the case of rotational scanning, there is generally projected onto the eye OE a beam whose transverse cross-section is caused to rotate about the projection axis O, which is of course substantially coincident with the optical axis of the eye to be treated. The cross-section of the treatment laser beam FLT is of elongate shape, of course, and in a particularly advantageous way has at least one or several lobes as defined previously. The generatrix at the end of the treatment laser beam or the corresponding lobe coincides with the rotation axis O in FIG. 2a. The ablation is done by applying the beam to a large number of successive angular positions, spaced by the appropriate angular increment of rotation about the axis O. To obtain the required correction the cross-section of the treatment laser beam FLT, the energy density per unit surface area of which is substantially constant, has the profile as defined previously on the basis of the object slits 211.

In the second embodiment, in particular using the device as shown in FIG. 4a, the resulting total ablation is obtained by scanning the treatment laser beam FLT in translation by successive linear increments. The displacement takes place in the direction perpendicular to the longitudinal dimension of the largest dimension of the lobe of the laser beam FLT and perpendicular to the optical axis O of the eye OE. Several operations are needed to carry out a complete treatment.

Of course, and in a non-limiting way, it is possible to carry out several operations, for example, the treatment laser beam FLT undergoing after each pass a rotation of a fraction of a circle about the optical axis O. After n passes (n/2 if the beam is symmetrical), the combination of the aforementioned operations produces an nth order circular symmetry ablation more or less approximating the required effect.

A particularly advantageous instance, as previously described, is the use of a beam of parabolic cross-section the lobes of which have a parabolic shape as described previously, the laser beam being scanned in two passes along two perpendicular directions.

Compared with rotational scanning of the treatment laser beam FLT, scanning in translation for correction of myopia avoids a problem specific to rotary scanned beams, namely that the centre of the eye where the ablation is strongest coincides with the centre of rotation and that the latter is situated by design at an end of the impact area. In the event of any error in aligning this impact area with respect to the rotation axis, total absence of ablation (or its opposite, excessive ablation) may result in the immediate vicinity of the centre of the cornea. This problem is absent in the case of beams scanned in translation.

Furthermore, in the case of scanning in translation the choice of this scanning mode (along two orthogonal directions) provides a simple means of correcting astigmatism. For this, it is sufficient for the two orientations of the beam along the directions OX and OY to coincide with the principal directions of astigmatism. It then suffices to change the average density of exposure by changing the length of the linear increments between the two orthogonal passes to obtain an ablation of elliptical rather than circular symmetry.

The translational scanning treatment laser beams may of course be used in various ways, the beams with different orientations being applied either successively or simultaneously.

Another particularly advantageous embodiment of an object slit 211 and a diaphragm 21 will be described with reference to FIGS. 6a through 6d.

Figure 6A:
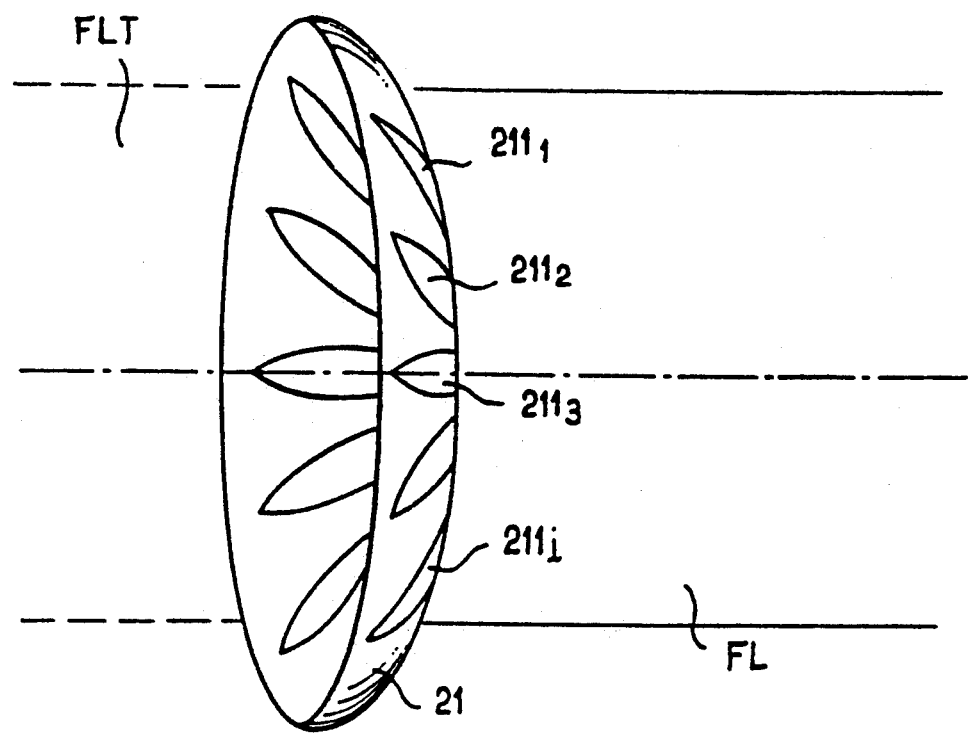
Figure 6B:
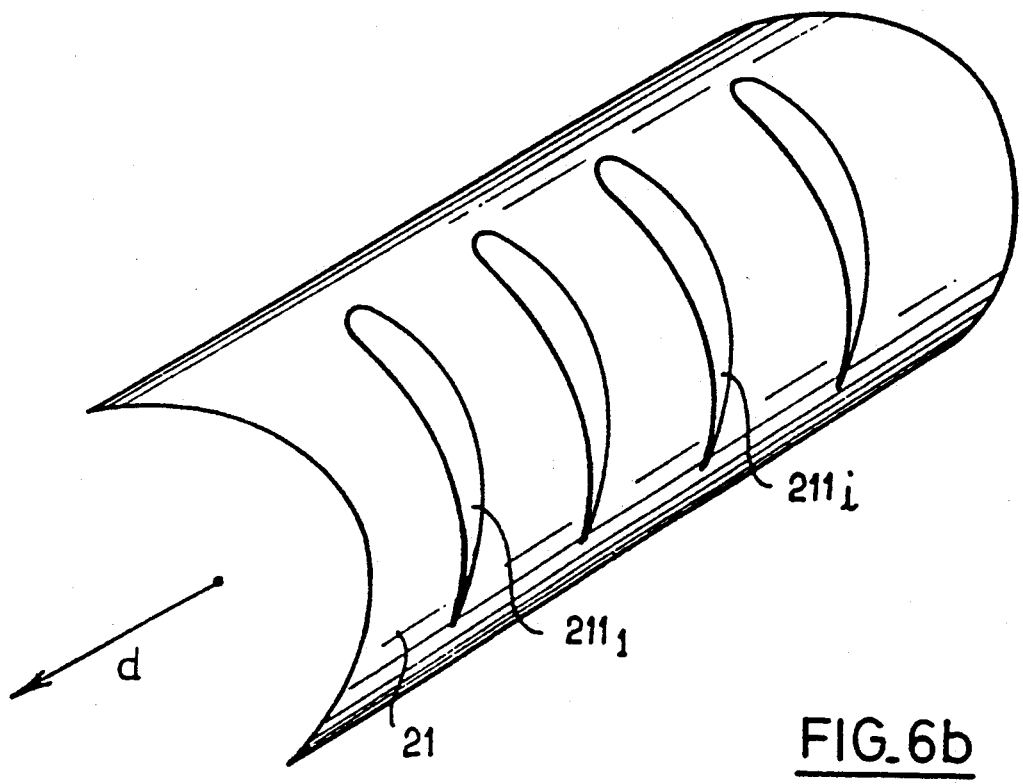

Referring to FIG. 6a and FIG. 6b, the object slits as previously shown in FIGS. 3b, 3c, 3d, 3e, 3f, 4b, 4c and 4d may advantageously be formed on a diaphragm 21 with a curved surface matching the surface of the cornea COR. This embodiment improves the quality of focussing of the image of the object slit on the cornea COR. In the case of FIG. 6a, the curved surface forming the diaphragm 21 is a spherical dome and the diaphragm may be rotated about its axis of symmetry, as previously described. In the case of object slits scanned in translation, the curved surface forming the diaphragm 21 may advantageously, and as shown in FIG. 6b, be a semicylindrical surface the longitudinal axis of which is oriented in the translation direction d, the object slits having their axis O″z perpendicular to the longitudinal axis of the aformentioned half-cylinder.

A particularly advantageous embodiment of the diaphragm 21 will be described with reference to FIGS. 6c, 6d and 6e.

In the aforementioned FIG. 6c the diaphragm 21 comprises a semicylindrical surface of radius R with a longitudinal axis O‴x. The semi-cylindrical surface has an object slit 211 with an aperture or width in the direction O‴x denoted E(φ). The aperture is, for example, symmetrical to a plane P orthogonal to the longitudinal axis O‴x, this plane containing the directions O‴y and O‴z orthogonal to the direction of the longitudinal axis O‴x. In FIG. 6c, S represents the middle of the aperture or the width of the slit at a height z corresponding to a given angle φ, the angle φ being defined as the angle between the radius vector O‴S of a point S on the geometrical locus LS, the curve of symmetry of the object slit 211, and the direction 0y. The width E(φ) of the object slit 211 satisfies the equation:

$$E(\phi) = E\frac{(\pi)}{2} \sin^3\phi \tag{39}$$

In this equation, $E(\pi/2)$ represents the maximum width or aperture of the object slit 211 for $\phi = \pi/2$.

It will of course be noted, as will be described in more detail later, that in the case of an operation by keratomileusis to cure myopic astigmatism the radius R of the semicylindrical surface constituting the diaphragm 21 determines the area within which the practitioner operates on the cornea COR. To give a non-limiting example, the aforementioned radius is taken as equal to the operating area, the magnification of the focussing optics being taken as equal to unity. It is obvious that any semicylindrical diaphragm of appropriately similar shape could be used, the magnification of the focussing optics being adapted accordingly.

To correct the cornea COR by keratomileusis for myopic astigmatism, for example, the diaphragm 21 as shown in FIG. 6c is disposed relative to the cornea COR so that its concave side faces towards the area of the latter to be treated. The cornea COR is assumed to have a circular surface of radius R' and the object slit 211 as shown in FIG. 6c is illuminated by the laser beam FL. The longitudinal axis O‴x and the transverse axis P‴y of the diaphragm are oriented in the principal directions of astigmatism OX, OY of the cornea COR, these principal directions having been determined beforehand by the practitioner.

The device in accordance with the invention further comprises drive means 400 for rotating the diaphragm 21 about the axis O‴y, the rotation drive means 400 advantageously comprising a stepper motor and two rotation half-shafts 401, 402 driven by the latter.

Figure 6D:
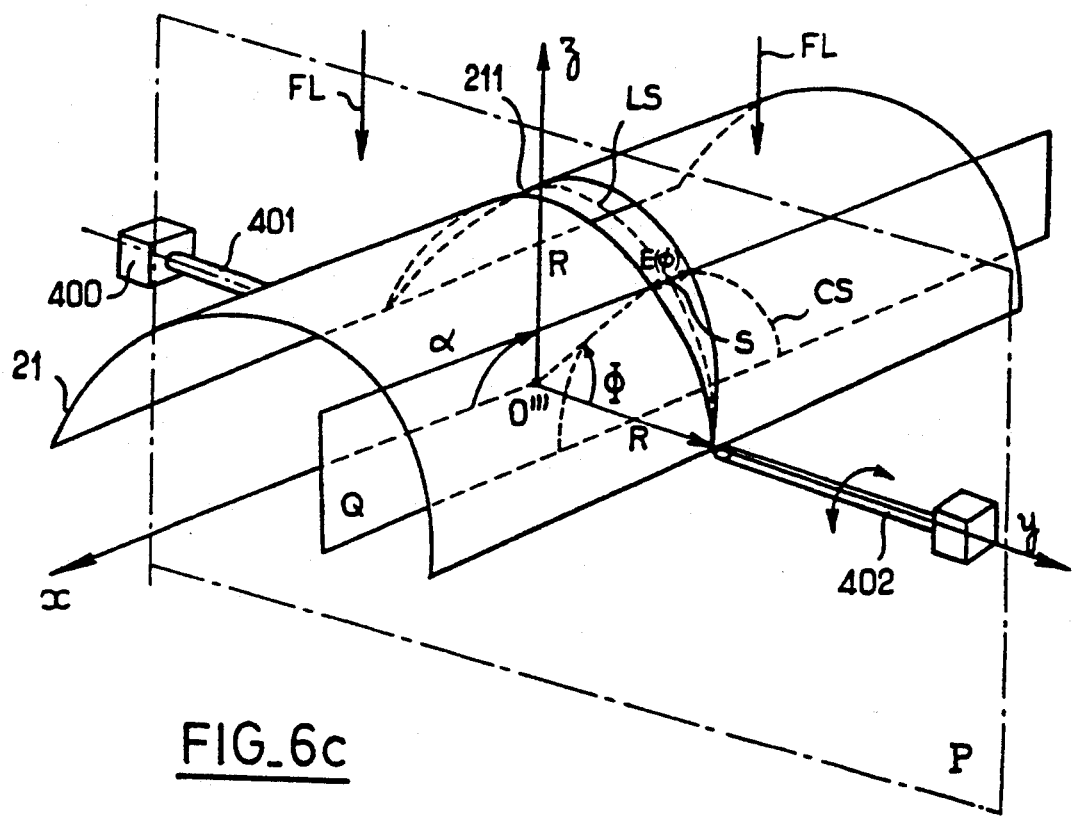
Figure 6D:
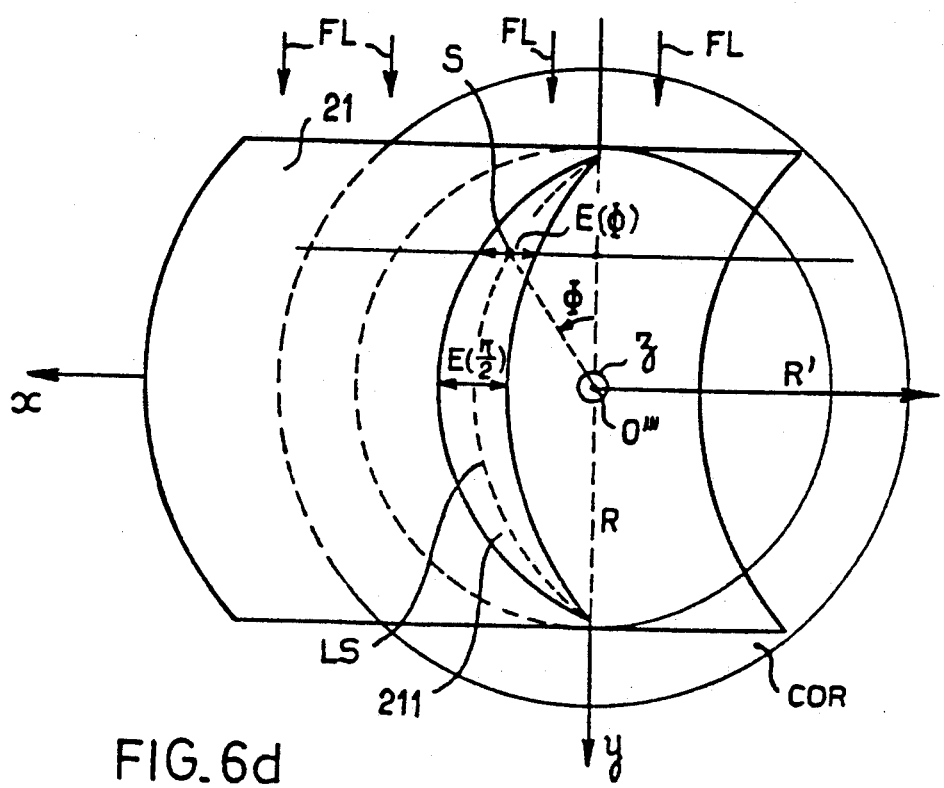

As will be noted on observing FIGS. 6c, 6d and 6e, the width E(φ) of the object slit 211 which is also shown in FIG. 6c by the intersection of the slit and a plane Q for which the equation is Y=R Cosφ, is projected on the axis OX as an image of width E (α,φ) when the slit 211 is illuminated with parallel light, for example. The width of the slit projected on the axis OX satisfies the equation:

$$E'(\alpha,\phi) = E(\phi) \cdot \sin \alpha \tag{40}$$

In this equation, α represents the angle of inclination by which the diaphragm 21 is rotated and in particular of the axis O‴z thereof relative to the direction OX. The slit 211 turns substantially on a sphere with the same radius as the cylinder and, as the diaphragm 21 is rotated, any middle point S at a height z corresponding to a given angle φ performs a circle CS in the aforementioned plane Q, as shown in FIGS. 6c and 6e.

If it is assumed that the ablation function A(α,φ) corresponds to the ablation function A(X,Y) defined by equation (34) and is proportional to the number of pulses received for an elementary displacement less than E'(α,φ) and therefore less than the width E'(α,φ) of the image of the slit on the axis OX divided by the elementary displacement Δx(α) (along the OX axis) for each laser pulse, we may write:

$$X(\alpha) = R\sin\phi \, \cos\alpha \text{ and } \frac{\delta X}{\delta \alpha} \cdot d\alpha = \frac{\delta}{\delta \alpha} R\sin\phi \, \cos\alpha \, d\alpha =$$

$$-R\sin\phi \, \sin\alpha \, d\alpha \text{ and } \Delta X(\alpha) = R \sin\phi \, \sin\alpha \Delta\alpha$$

whence

-continued $$A(X,Y) = A(\alpha,\phi) = \frac{E'(\alpha,\phi)}{\Delta X(\alpha)}$$

that is $$A(\alpha,\phi) = \frac{(E)\phi}{R\sin\phi\Delta\alpha} \quad (41)$$

Given the chosen ablation function A(X,Y) defined by equation (34) above, OX and OY are chosen such that Rx≦Ry and R is chosen such that R=Ry as shown in FIGS. 6d and 6e in particular.

Using the same notation as previously, the ablation function may be written:

$$A(X,Y) = \frac{A0}{2}\left(1 - \frac{X^2}{R_x^2} - \frac{Y^2}{R^2}\right) \quad (42)$$

Given the equations:
X = R sinφ cosα
Y = R cosα
the ablation function becomes:

$$A(X,Y) = A(\alpha,\phi) = \frac{A0}{2}\left(1 - \frac{R^2}{R_x^2}\cos^2\alpha\right)\sin^2\phi \quad (43)$$

Given equations (41) and (43) above, the ablation function may be related to the law of the aperture of the slit E(φ) and the rotation increment Δα by the equation:

$$\frac{E(\phi)}{\Delta\alpha} = \frac{RA0}{2} \cdot \sin^3\phi \cdot \left(1 - \frac{R^x}{R_x^2}\cos^2\alpha\right) \quad (44)$$

It then suffices to choose:

$$E(\phi) = E\frac{(\pi)}{2}\sin^3\phi$$

and $$\Delta\alpha = \Delta 0\left(1 - \frac{R^2}{R_x^2}\cos^2\alpha\right)^{-1}$$

Choosing E(π/2) and Δ0 for a given semicylindrical diaphragm produces the required profile.

By modulating the angular rotation increment Δα, the previously described embodiment can correct astigmatism of the cornea and myopia without any problems of edge discontinuities at the periphery of the correction area or excessive ablation at the centre of the cornea. The junction between the corrected area and the uncorrected area is perfect. Also, in the absence of any astigmatism the previous equations hold, given that Rx=Ry=R. In all cases, the X and Y ablation functions depend only on α and φ respectively.

To facilitate use of the device in accordance with the invention as shown in FIG. 3a or in FIG. 4a the calculation means 8 may comprise a microcomputer 80 with its peripheral devices. The memory areas of the microcomputer store programs and/or subroutines for calculating the numbers of laser pulses NI$_1$, NI$_2$ previously mentioned in the description, the total irradiation times T$_{1min}$, T$_{2min}$, and sub-routines for sequencing and synchronising the displacement of the treatment laser beam FLT. These sequencing programs are used, for example, to generate rotation or translation displacement commands scdr and scdt and laser emission commands sce. The program or subroutine can also include a program for modulating the rotation increment Γ as a function of the azimuth angle β or the translation increment Δu as a function of the value of the X or Y ascissa of the rotation increment Δα.

To facilitate the work of the practitioner the microcomputer 80 may further comprise in its memory area a "menu" type program inviting the practitioner, through an interactive type dialogue, to define at least the principal directions of astigmatism of the eyeball relative to a reference marker, the principal directions having been established by the practitioner as a result of a diagnosis.

The "menu" program may advantageously also invite the practitioner to specify the value of the parameter R defining the optical area for operation and correction of the cornea COR. It may also invite the practitioner to designate the treatment method i.e. scanning the object slits or images of the object slits in rotation or in translation. Finally, the type of operation may be specified according to the particular case under treatment.

The microcomputer 80 can of course be connected by a BUS type link to the means 5 for synchronising the displacement of the image of the lobe or lobes of the treatment laser beam FLT. The means 5 for synchronising the displacement of the image may advantageously comprise an input/output interface circuit generating from rotation or translation displacement commands scdr and scdt and emission commands sce respective commands SCDR, SCDT, SCE for the displacement control means 4 and the laser emission means 1. The input/output interface circuit will not be described in detail, as it may be provided by any conventional type interface with provision for controlling the stepper motor in particular.

Finally, to facilitate the work of the practitioner, following his diagnosis, the device in accordance with the invention may comprise a set of diaphragms each comprising an object slit 211 as defined and described with reference to FIGS. 3b, 3c, 3d, 3e, 3f, 4b, 4c, 4d, 4e, 6a, 6b, and 6c.

There has thus been described a device for performing surgery on the cornea in which rotational or translational scanning of a laser beam having at least one lobe of elongate cross-section produces a precise law of ablation over the area of the cornea COR of the eye to be corrected. Laboratory tests have shown that, compared with prior art devices in which the depth of ablation was controlled by the time of exposure to the treatment laser beam, the corrected surfaces after treatment, that is to say the surfaces of the cornea serving as the input optical surface of the eye of the patient, show a much reduced degree of roughness, thus conferring superior optical qualities on the surfaces of the treated cornea. It has been observed that the degree of roughness of the surfaces after treatment does not exceed 1 μm. The degree of roughness of the corneal surfaces after treatment with the prior art devices may be explained by the fact that these devices have the disadvantage of applying the laser emission power simultaneously to the major part of the cornea, the effect of which is to create an acoustic shock wave resulting from simultaneous vapourising of material over the anterior surface of the cornea. This kind of phenomenon can also have unwanted physiological consequences, such as ejection of endothelium cells, for example. The device in accordance with the invention makes it possible to eliminate the disadvantages of these devices since the resulting total ablation when the device in accordance with the invention is used results from the summation of elementary ablations distributed over the cornea according to precise mathematical laws, each elementary ablation being carried out with minimal energy density.

Figure 7:
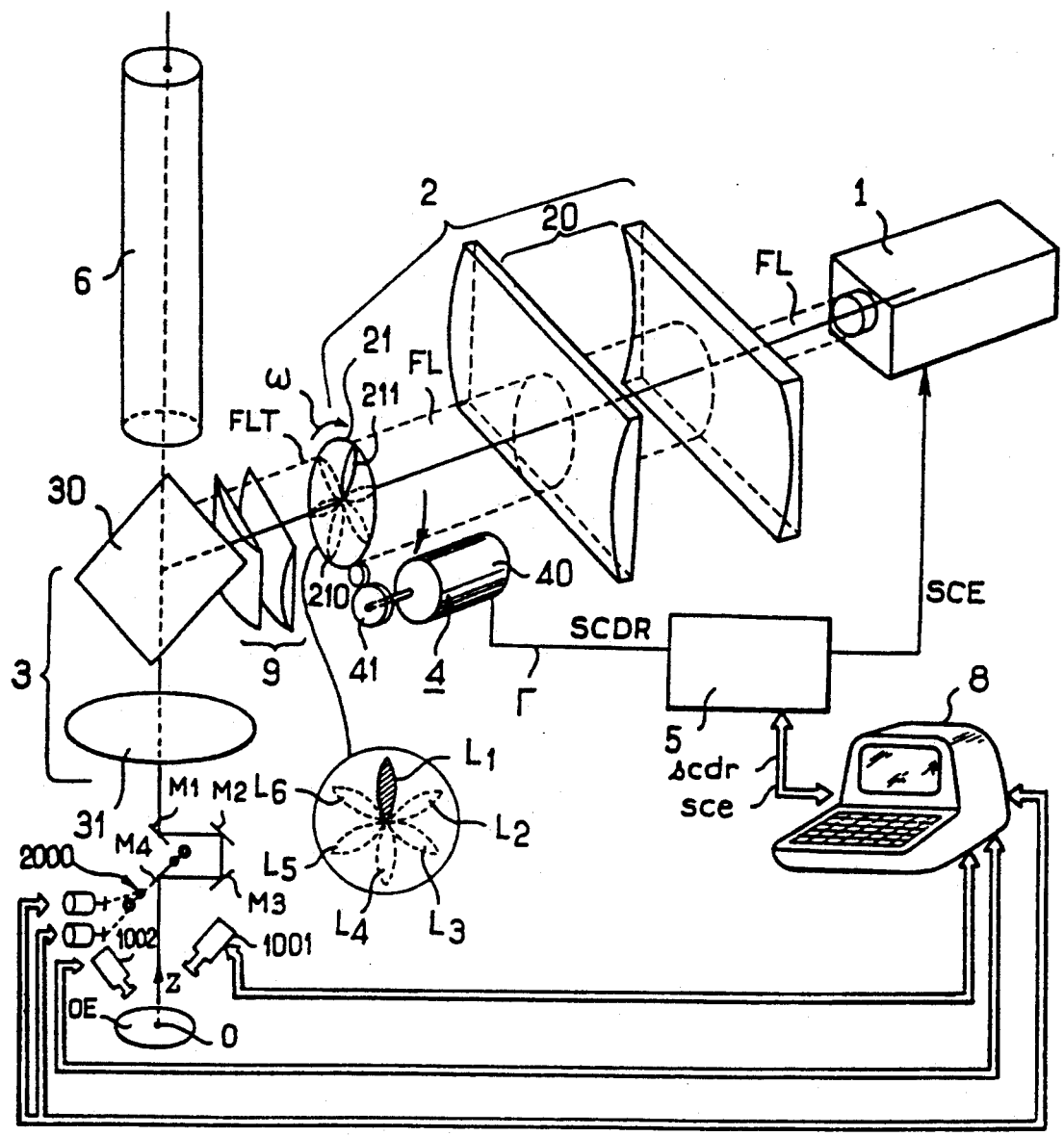

Of course, the device in accordance with the invention is not limited to refractive eye surgery. It may also constitute a device for shaping or correcting the shape of an object by laser treatment of the surface of the object. In this case, the device comprises the means 2 for generating a treatment laser beam FLT comprising at least one lobe L1 ... L6 of elongate cross-section and means 3 for focussing the image of the lobe or lobes of the treatment laser beam FLT onto the area of the object OE to be corrected. The means 4 for moving the image of the lobe or lobes of the treatment laser beam FLT over the area of the object to be corrected serve to move the latter over the area of the object to be corrected. The means 5 for synchronising movement of the image of the lobe or lobes of the treatment laser beam FLT over the area of the object OE to be corrected with the treatment laser beam pulses serve to perform the correction or shaping by summing a plurality of elementary discrete ablations. As shown in FIG. 7, the image of the lobe or lobes of the laser beam is focussed in such a way that the generatrix of one end of the lobe or lobes or the longitudinal axis of symmetry of a lobe or the lobes of the laser beam FLT is coincident with the axis of symmetry OZ of the object to be treated or of an elementary surface of the object to be treated. The means 4 for moving the image of the lobe or lobes of the treatment laser beam FLT over the area of the object to be corrected serve to move the image of the lobe or lobes L1 ... L6 of the laser beam in rotation about the end generatrix or the longitudinal axis of symmetry of the lobes of the treatment laser beam FLT. The rotation is applied in rotation angle increments. The device corresponds substantially to the embodiment of FIG. 3a.

Furthermore, in an embodiment corresponding to that of FIG. 4a of a device for shaping or correcting the shape of an object by laser treatment, the means 4 for moving the image of the lobe or lobes of the treatment laser beam FLT over the area of the object to be treated provide for movement in translation in a direction d substantially perpendicular to the largest dimension 0z of the lobe of the treatment laser beam FLT. The movement in translation may be effected in displacement increments $\Delta u$, the movement in translation being defined by $u = X$ or $u = Y$ defining a plane tangential to the surface of the object OE at the point 0 on the axis of symmetry of the object or an elementary area of the latter to be treated.

A non-limiting alternative embodiment of the device in accordance with the invention for shaping or correcting the shape of an object or for performing refractive eye surgery will be described with reference to FIG. 7, this embodiment being based on the embodiment of FIG. 3a or FIG. 4a. Referring to FIG. 7, the device in accordance with the invention further comprises a real time shape recognition system comprising at least two video cameras 1001, 1002 viewing the object or the eye OE to be treated and transmitting image data to the calculation means 8. The video cameras 1001, 1002 allow for monitoring the progress of the shaping or correction of the object during the treatment process. The shape recognition means may comprise shape recognition means available through normal trade channels and will not be described in detail.

As shown in FIG. 7, a series of mirrors M1, M2, M3, M4 deflect the treatment laser beam FLT. At least one of these mirrors, the mirror M4, is mounted on a gimbal 2000. The two frames of the gimbal mounting are shown in cross-section in FIG. 7 to avoid over-complicating the drawing. Drive and orientation adjustment means for the adjustment mirror comprise DC or stepper motors, for example. These motors are controlled by the shape recognition means 1001, 1002 through the intermediary of the calculating means 8, using a bus type link. The shape recognition system therefore serves to monitor the progress of the correction or treatment during the process and to control the deflection of the treatment laser beam FLT by means of the mirror M4 in the event of uncontrolled movement of the object or of the eye of the patient. In the latter case the practitioner can advantageously make coloured marks on the cornea of the patient before the treatment begins, using methylene blue, for example. Note, however, that if an arrangement of this kind is used with the device in accordance with the invention as shown in FIG. 4a, the shape recognition means 1001, 1002 can control the focussing lens 430 directly by means of an X-Y movable table 43.

The device in accordance with the invention is therefore usable for shaping or correcting the shape of mechanical objects such as contact lenses or intra-ocular implants and for refractive eye surgery.

There is claimed:

1. Device for shaping the shape of an object by laser ablation of a surface of said object according to an ablation function A (X,Y), where said object has dimensions in X and Y directions, said X and Y directions are orthogonal directions, values of X and Y are less than the dimension of said object in said X and Y directions, that is to say the thickness to be removed at point of X, Y coordinates on reference axes OX, OY of said surface, O being the center of said object, said ablation function being written as:

$$A(X,Y) = A_X(X) + A_Y(Y)$$

where $A_X(X)$ and $A_Y(Y)$ represent the respective ablation functions on said reference axes OX and OY, said device comprising:

means for generating a pulses laser beam having pulses and a stable energy density;

means for assuring homogeneity of said energy density;

first slit means for limiting laser radiation passing therethrough, said slit means having at least one slit oriented in the X direction and intercepting said laser beam, said slit having a profile function E (X) given by:

$$E(X) = \frac{\Delta X_Y}{\bar{a}(e)} \cdot A_X(X)$$

where $\Delta X_Y$ is a non-zero translation displacement increment in the Y direction and $\bar{a}$ (e) represents the average thickness removed by irradiation of each laser pulse;

second slit means for limiting laser radiation passing therethrough, said slit means having at least one slit oriented in the Y direction and intercepting said laser beam, said slit having a profile function E (Y) given by:

$$E(Y) = \frac{\Delta Y_X}{\bar{a}(e)} \cdot A_Y(Y)$$

where $\Delta Y_X$ is a non-zero translation displacement increment in the X direction;

means for forming an image of said slits onto an area of said surface of said object;

means for displacing said image of said first slit means slit over said area in the Y direction by steps of increment $\Delta X_Y$, corresponding to elementary discrete ablations of said surface of said object;

means for displacing said image of said second slit means slit over said area in the X direction by steps of increment $\Delta Y_X$, corresponding to elementary discrete ablations of said surface of said object; and means for synchronizing said increments, said pulses and said energy density, so that the total ablation resulting from the summation of said elementary discrete ablations meets said ablation function A (X,Y).

2. Device according to claim 1, for refractive eye surgery, wherein said surface of said object is an external surface of the cornea of an eye and in order to compensate for astigmatism of the eye by re-establishing the symmetry of revolution of said cornea, said X and Y directions are respectively oriented along major and minor axes of astigmatism.

3. Device according to claim 1, wherein said means for displacing said image of said slits comprises:
   a diaphragm comprising said slits;
   a first lens, said slits located at an object focal plane of said first lens; and
   a second focusing lens mobile in translation in one of said X and Y directions.

4. Device according to claim 3, further comprising a rotating prism, located between said first and second lens, for enabling rotation of said slit direction about an axis of said surface of said object.

5. Device according to claim 1, for refractive eye surgery, wherein said surface of said object is the external surface of the cornea of an eye and, for treatment of myopia, said ablation function $A_u(u)$ satisfies the equation:

$$A_u(u) = 2A_u^0 \left( \frac{1}{2} - \frac{u^2}{R^2} \right)$$

where u is one of X and Y, $A_u^\circ$ is the maximum value of said ablation function, and R represents the radius of said cornea.

6. Device according to claim 5, for refractive eye surgery, wherein said surface of said object is the external surface of the cornea of an eye and for treatment of myopic astigmatism, said reference axes OX, OY are taken parallel to principal astigmatism directions and said maximum values $A_X^\circ$ and $A_Y^\circ$, respectively, depend on the radius of curvature of the cornea along the OX and OY axes.

7. Device according to claim 1, for refractive eye surgery, wherein said surface of said object is the external surface of the cornea of an eye and wherein, for treatment of hypermetropia, said ablation function $A_u(u)$ satisfies the equation:

$$A_u(u) = A_u^0 \cdot \frac{u^2}{v^2} \text{ where } 0 \leq |u| \leq v \ (v < R)$$

where u is one of X and Y, $A_u^\circ$ is the maximum value of said ablation function, and R represents the radius of said cornea.

8. Device according to claim 7, for refractive eye surgery, wherein said surface of said object is the external surface of the cornea of an eye and for treatment of hypermetropic astigmatism, said reference axes $O_X$, $O_Y$ are taken parallel to principal astigmatism directions and maximum values $A_X^\circ$ and $A_Y^\circ$, respectively, depend on the radius of curvature of the cornea along the OX and OY axes.

9. Device according to claim 1, further comprising means for calculating the translation displacement increment $\Delta u_v$ which satisfies the equation:

$$\Delta u_v = E_{max} \cdot \frac{\bar{a}_u(e)}{A_u^0}$$

where (u, v) represent one of (X,Y) and (Y,X), $E_{max}$ represents the maximum width of said profile function of said slit oriented in the u direction, and $A_u^\circ$ is the maximum value of said ablation function $A_u(u)$.

10. Device according to claim 9, further comprising means for calculating the number $NI_2^v$ of laser pulses and the number of translation displacement $\Delta u_v$ in the v direction, the number $NI_2^v$ of pulses satisfying the equation:

$$NI_2^v = ND_2^v \cdot \frac{A_u^0}{\bar{a}_u(e)}$$

where $ND_2^v$ represents the number of totally separate image of said slit in the v direction.

11. Device according to claim 10, further comprising means for calculating the minimum total irradiation time $T_{2min}^v$ in the v direction which satisfies the equation:

$$T_{2min}^v = NI_2^v \cdot \frac{\tau^v(e)}{ND_2^v} = \tau^v(e) \cdot \frac{A_u^0}{\bar{a}_u(e)}$$

where $\tau^v(e)$ represents the minimum time interval between two successive irradiations of a same point of said area in the v direction.

12. Device according to claim 1, wherein said slit of each slit means is formed on a diaphragm forming a semicylindrical surface of radius R with a longitudinal axis $O'''x$, said slit having a profile function $E(\phi)$ in the direction $O'''x$ symmetrical with respect to a plane orthogonal to the longitudinal axis $O'''x$, said plane containing directions $O'''y$ and $O'''y$ and $O'''z$ orthogonal to the direction of said longitudinal axis $O'''x$, said profile function $E(\phi)$ satisfying the equation:

$$E(\phi) = E\left(\frac{\pi}{2}\right) \sin^3 \phi$$

where $\phi$ represents the angle of a radius vector of a point on a curved geometrical locus of symmetry of said slit and of said direction O'''Y, and $E(\pi/2)$ represents a maximal profile function of said slit for $\phi=\pi/2$.

13. Device according to claim 12 for refractive eye surgery wherein said surface of said object is the external surface of the cornea of an eye and, in order to compensate for astigmatism of the eye by re-establishing symmetry of revolution of said cornea, said diaphragm has a concave side facing towards said cornea and said slit is adapted to be illuminated by said laser beam, said longitudinal axis O'''x and said transverse axis O'''y of said diaphragm being oriented in the principal directions of astigmatism of said cornea, said device further comprises drive means for rotating said diaphragm about said axis O'''y.

14. Device according to claim 13, further comprising drive means for rotating said diaphragm about said axis O'''y, consisting of a stepper motor enabling said diaphragm to be rotated in rotation displacement increments $\Delta\alpha$ satisfying the equation:

$$\Delta\alpha = \Delta0 \left( 1 - \frac{R^2}{R_x^2} \cos^2 \alpha \right)^{-1}$$

where $\alpha$ represents the inclination of said diaphragm and of said axis O'''z relative to said reference direction OX, $\Delta O$ represents the minimum angular rotation increment for $\alpha=\pi/2$, and R and $R_x$ are the radii of cornea respectively for $\alpha=0$ and $\alpha=\pi/2$.

15. Device according to claim 14, said drive means further comprising means:
for calculating the rotation translation displacement increment $\Delta\alpha$ which satisfies the equation:

$$\Delta\alpha = \Delta0 \left( 1 - \frac{R^2}{R_x^2} \cos^2 \alpha \right)^{-1}$$

where $\alpha$ represent the inclination of said diaphragm and of said axis O'''z relative to said reference direction OX, $\Delta O$ represents the minimum angular rotation increment for $\alpha=\pi/2$, and R and $R_x$ are the radii of cornea respectively for $\alpha=0$ and $\alpha=\pi/2$; and
for applying $\Delta\alpha$ to said stepper motor.

* * * * *

UNITED STATES PATENT AND TRADEMARK OFFICE
CERTIFICATE OF CORRECTION

PATENT NO. : 5,284,477
DATED : February 8, 1994
INVENTOR(S) : Hanna, et. al.

It is certified that error appears in the above-indentified patent and that said Letters Patent is hereby corrected as shown below:

Title page, item [73], Assignee: should read--International Business Machines Corporation, Armonk, N.Y.  Khalil Hanna, Paris, France--.

Signed and Sealed this

Ninth Day of May, 1995

Attest:

BRUCE LEHMAN

Attesting Officer

Commissioner of Patents and Trademarks